(12) United States Patent
Czerkinsky et al.

(10) Patent No.: US 8,168,203 B2
(45) Date of Patent: May 1, 2012

(54) ***SHIGELLA* PROTEIN ANTIGENS AND METHODS**

(75) Inventors: Cecil Czerkinsky, Seoul (KR); Dong Wook Kim, Seoul (KR)

(73) Assignee: International Vaccine Institute, Seoul (KR)

( * ) Notice: Subject to any disclaimer, the term of this patent is extended or adjusted under 35 U.S.C. 154(b) by 0 days.

(21) Appl. No.: 12/692,187

(22) Filed: Jan. 22, 2010

(65) Prior Publication Data

US 2010/0136045 A1   Jun. 3, 2010

Related U.S. Application Data

(62) Division of application No. 12/603,574, filed on Oct. 21, 2009.

(60) Provisional application No. 61/107,306, filed on Oct. 21, 2008.

(51) Int. Cl.
*A61K 39/02* (2006.01)
*A61K 39/00* (2006.01)
*A61K 39/38* (2006.01)

(52) U.S. Cl. ............ 424/234.1; 530/300; 530/350; 435/41; 435/71.1; 435/243; 424/9.1; 424/9.2; 424/184.1; 424/185.1; 424/190.1; 424/193.1; 424/197.11

(58) Field of Classification Search .......... 424/9.1, 424/9.2, 184.1, 185.1, 190.1, 193.1, 197.11, 424/234.1; 435/41, 71.1, 243; 530/300, 530/350
See application file for complete search history.

*Primary Examiner* — Rodney P. Swartz
(74) *Attorney, Agent, or Firm* — Knobbe, Martens, Olson & Bear, LLP

(57) ABSTRACT

The present invention relates to protein antigens IcsP2 and SigA2 from *Shigella* that are common among numerous *Shigella* types and species and which can protect against shigellosis or other enteric infections when administered as vaccines. In addition, the present invention relates to antigens that are in common between *Shigella* species and enteroinvasive *Escherichia coli* (EIEC). The invention also relates to the use of antibodies raised against these antigens and of DNA probes for use in the diagnosis of *Shigella* and EIEC infections.

10 Claims, 19 Drawing Sheets

Invasive *S. flexneri* 2a | *S. flexneri* 2a mixed with anti-SigA2

FIGURES 9A-B

M: marker, 1:S. *flexneri* (2a 2457T), 2:S. *boydii*, 3:S. *dysenteriae* type 1, 4:S. *sonnei*, A:SigA2, B:IcsP2

2457T
(2x10⁴CFU)

2457T+SIgA2
anti-serum
(2x10⁴CFU)

Fig. 12A
IcsP2 sequence of the full length IcsP protein is depicted. The nucleotide (SEQ ID NO:1) and amino acid sequences (SEQ ID NO:2) of the IcsP2 portion are indicated in the boxed region.

```
  1 - ATGAAATTAAAATTCTTTGTACTTGCACTTTGTGTACCTGCGATCTTTACTACACATGCT  -  60
  1 - M  K  L  K  F  F  V  L  A  L  C  V  P  A  I  F  T  T  H  A  -  20

61 - ACCACTAACTATCCACTTTCATCGGACACATCGGATATTAGTCTAGGATCT          - 120
 21 - T  T  N  Y  P  L  F  I  P  D  N  I  S  T  D  I  S  L  G  S  -  40

121 - CTGAGTGGCAAAACAAAAGAACGCGTTTATCATCCCAAGGAAGGGGAGAAAAATTAGT   - 180
 41 - L  S  G  K  T  K  E  R  V  Y  H  P  K  E  G  G  R  K  I  S  -  60

181 - CAACTGGACTGGAAATACAGTAATGCCACTATTGTTAGAGGTGGCATCGATTGGAAGCTA - 240
 61 - Q  L  D  W  K  Y  S  N  A  T  I  V  R  G  G  I  D  W  K  L  -  80

241 - ATTCCAAAAGTGTCTTTCGGAGTTTCCGGTTGGACTACTTTAGGTAACCAGAAAGCAAGC - 300
 81 - I  P  K  V  S  F  G  V  S  G  W  T  T  L  G  N  Q  K  A  S  - 100

301 - ATGGTTGATAAAGACTGGAACAATTCCAATACCCCTCAGTATGGACCGACCAGAGCTGG  - 360
101 - M  V  D  K  D  W  N  N  S  N  T  P  Q  V  W  T  D  Q  S  W  - 120

361 - CATCCCAATACGCATCTCCGTGATGCTAACGAATTCGAGCTGAATCTTAAAGGTTGGTTA - 420
121 - H  P  N  T  H  L  R  D  A  N  E  F  E  L  N  L  K  G  W  L  - 140

421 - TTAAATAATTTGGATTATCGACTTGGACTTATAGCAGGTTACCAAGAGAGTCGTTACAGT - 480
141 - L  N  N  L  D  Y  R  L  G  L  I  A  G  Y  Q  E  S  R  Y  S  - 160

481 - TTTAATGGAGGGAGTTATATTTATAGTGAAAACGGGGAGCAGGAATAAAAAA         - 540
161 - F  N  G  G  S  Y  I  Y  S  E  N  G  G  S  R  N  K  K        - 180

541 - GGGGCACATCCTAGTGGTGAAAGAACAATAGGTTACAAACAGCTCTTCAAAATACCTTAT - 600
181 - G  A  H  P  S  G  E  R  T  I  G  Y  K  Q  L  F  K  I  P  Y  - 200

601 - ATTGGATTAACTGCTAATTACCGCCATGAGAATTTTGAGTTTGGAGCAGAACTGAAATAT - 660
201 - I  G  L  T  A  N  Y  R  H  E  N  F  E  F  G  A  E  L  K  Y  - 220

661 - AGTGGTTGGGTTCTTTCATCTGATACAGATAAACACTATCAGACTGAGACAATTTTTAAA - 720
221 - S  G  W  V  L  S  S  D  T  D  K  H  Y  Q  T  E  T  I  F  K  - 240
```

Fig. 12B
IcsP2 sequence of the full length IcsP protein is depicted. The nucleotide (SEQ ID NO:1) and amino acid sequences (SEQ ID NO:2) of the IcsP2 portion are indicated in the boxed region.

```
721 - GATGAAATAAAAAACCAAAATTACTGCTCTGTTGCTGCGAATATTGGATACTATGTCACC - 780
241 -  D   E   I   K   N   Q   N   Y   C   S   V   A   A   N   I   G   Y   Y   V   T  - 260

781 - CCCAGTGCAAAATTTATAGAAGGCTCCAGAAATTACATTTCTAATAAAAAAGGTGAT - 840
261 -  P   S   A   K   F   Y   I   E   G   S   R   N   Y   I   S   N   K   K   G   D  - 280

841 - ACATCTCTTTATGAGCAAAGTACCAATATATCTGGCACCATTAAAAATAGTGCAAGTATT - 900
281 -  T   S   L   Y   E   Q   S   T   N   I   S   G   T   I   K   N   S   A   S   I  - 300

901 - GAATATATTGGTTTTCTCACTTCCGCAGGTATAAAGTATATTTTTGA - 948
301 -  E   Y   I   G   F   L   T   S   A   G   I   K   Y   I   F   *  - 320
```

Fig. 13A
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
  1 - ATGAATAAAATTTATTCACTGAAATAGTCATATTACAGGTGGATTAGTTGCTGTTTCT  -  60
  1 - M  N  K  I  Y  S  L  K  Y  S  H  I  T  G  G  L  V  A  V  S  -  20

61 - GAACTGACCCGGAAAGTTAGTGTCGGTACATCAGAAAGAAAGTTATCCTCGGTATTATT  - 120
 21 - E  L  T  R  K  V  S  V  G  T  S  R  K  K  V  I  L  G  I  I  -  40

121 - TTATCCTCAATATATGGAAGTTATGGCGAAACAGCATTTGCAGCAATGCTGGATATAAAT - 180
 41 - L  S  S  I  Y  G  S  Y  G  E  T  A  F  A  A  M  L  D  I  N  -  60

181 - AATATATGGACCCGCGATTATCTTGACCTTGCTCAAAACAGAGGAGAGTTCAGACCGGGT - 240
 61 - N  I  W  T  R  D  Y  L  D  L  A  Q  N  R  G  E  F  R  P  G  -  80

241 - GCAACAAATGTTCAATTAATGATGAAAGATGGAAAGATATTTCATTTTCCAGAACTACCT - 300
 81 - A  T  N  V  Q  L  M  M  K  D  G  K  I  F  H  F  P  E  L  P  - 100

301 - GTACCTGATTTTCTGCTGTTTCCAACAAGGTGCAACAACATCAATTGGAGGTGCGTAC   - 360
101 - V  P  D  F  S  A  V  S  N  K  G  A  T  T  S  I  G  G  A  Y  - 120

361 - AGTGTTACTGCGACTCATAACGGTACACAGCATCATGCAATAACAACAGTCATGGGAT   - 420
121 - S  V  T  A  T  H  N  G  T  Q  H  H  A  I  T  T  Q  S  W  D  - 140

421 - CAGACAGCATATAAAGCAAGTAACAGAGTATCATCTGGCAGTTTCGGTTCATCGTCTG   - 480
141 - Q  T  A  Y  K  A  S  N  R  V  S  S  G  D  F  S  V  H  R  L  - 160

481 - AATAAATTCGTCGTGAAAGATATGGCGTAAACTACAACGGTAAGGAACAAATAATTGGCTTC - 540
161 - N  K  F  V  V  E  T  T  G  V  T  E  S  A  D  F  S  L  S  P  - 180

541 - GAAGATGCGATGAAAAGATTCGGGTGTAAATTACAACGTAAGGAACAAATAATTGGCTTC - 600
181 - E  D  A  M  K  R  Y  G  V  N  Y  N  G  K  E  Q  I  I  G  F  - 200

601 - AGAGCAGGTGCCGGAACAACCTCAACGATATTAAACGGCAAACAATATCTGTTTGGACAA - 660
201 - R  A  G  A  G  T  T  S  T  I  L  N  G  K  Q  Y  L  F  G  Q  - 220

661 - AACTATAATCCCGACTGTTAAGCCAAGTCTTTTTAATCTGGACTGGAAAAACAAGAGT   - 720
221 - N  Y  N  P  D  L  L  S  A  S  L  F  N  L  D  W  K  N  K  S  - 240
```

Fig. 13B
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
 721 - TACATTATACCAACAGAACCCTTTTAAAAACTCACCAATTTTGGCGATAGTGGTTCT - 780
 241 -  Y  I  Y  T  N  R  T  P  F  K  N  S  P  I  F  G  D  S  G  G  S  - 260

781 - GGTTCTTATCTATATGATAAAGAACAACAAAAATGGGTTTTCCATGGTGTTACCAGTACA - 840
 261 -  G  S  Y  L  Y  D  K  E  Q  Q  K  W  V  F  H  G  V  T  S  T  - 280

841 - GTTGGTTTTATCAGTAGTACCAATATAGCCTGGACAAACTACTCGTTATTTAATAATATT - 900
 281 -  V  G  F  I  S  S  T  N  I  A  W  T  N  Y  S  L  F  N  N  I  - 300

901 - CTGGTAAACAATTTAAAAAAGAATTCACAAACACTATGCAGCTGGATGGTAAAAAACAA - 960
 301 -  L  V  N  N  L  K  K  N  F  T  N  T  M  Q  L  D  G  K  K  Q  - 320

961 - GAGTTATCATCGATTATAAAAGATAAGGACCTGTCTGTCTCAGGAGGAGGGTATTAACG - 1020
 321 -  E  L  S  S  I  I  K  D  K  D  L  S  V  S  G  G  G  V  L  T  - 340

1021 - CTCAAGCAGGATACCGATCTTGGCGGCATTGGCGGCTTATATTCGATAAGAACCAGACATAT - 1080
 341 -  L  K  Q  D  T  D  L  G  G  L  I  F  D  K  N  Q  T  Y  - 360

1081 - AAAGTGTACGGAAAAGATAAGTCTTATAAGGTGCCGGATAGATATTGATAATAATACC - 1140
 361 -  K  V  Y  G  K  D  K  S  Y  K  G  A  G  I  D  I  D  N  N  T  - 380

1141 - ACCGTTGAATGGAATGTTAAGGGCGTTGCCGGAGATAATCTGCATAAATAGTAGTGGT - 1200
 381 -  T  V  E  W  N  V  K  G  V  A  G  D  N  L  H  K  I  G  S  G  - 400

1201 - ACTCTGGATGTAAAAATAGCACAGGAGAAATAACCTAAAATAGGTAATGGGACTGTCATC - 1260
 401 -  T  L  D  V  K  I  A  Q  G  N  N  L  K  I  G  N  G  T  V  I  - 420

1261 - CTTAGTGCTGAAAAGCCTTCAATAAAATTTACATGCCGGAGGTACGGTAAAA - 1320
 421 -  L  S  A  E  K  A  F  N  K  I  Y  M  A  G  G  K  G  T  V  K  - 440

1321 - ATAAATGCCAAAGACGCTTTAAGCGAAATGGCGAAATCTATTTTACCAGAAAT - 1380
 441 -  I  N  A  K  D  A  L  S  E  S  G  N  G  E  I  Y  F  T  R  N  - 460
```

Fig. 13C
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
1381 - GGCGGAACACTGGATCTAAACGGCTATGACCAGTCATTTCAGAAAATCGCAGCAACAGAT - 1440
 461 -  G  G  T  L  D  L  N  G  Y  D  Q  S  F  Q  K  I  A  A  T  D  -  480

1441 - GCGGGAACAACCGTAACGTGAAGACTCAAACGTGAAGCAATCAACATTATCACTTACTAATACT - 1500
 481 -  A  G  T  T  V  T  N  S  N  V  K  Q  S  T  L  S  L  T  N  T  -  500

1501 - GATGCATATATGTACCATGGGAATGTATCAGTAATAGCATAAATCATATATTATCAAT - 1560
 501 -  D  A  Y  M  Y  H  G  N  V  S  G  N  I  S  I  N  H  I  I  N  -  520

1561 - ACTACCCAGCAACATAACATAATGCCAATCTGATCTTTGATGGCTCAGTCGATATCAAA - 1620
 521 -  T  T  Q  Q  H  N  N  N  A  N  L  I  F  D  G  S  V  D  I  K  -  540

1621 - AACGATATCTCTGTCCGGAATGCACAGTTAACATTACAAGGACATGCGACAGAACATGCC - 1680
 541 -  N  D  I  S  V  R  N  A  Q  L  T  L  Q  G  H  A  T  E  H  A  -  560

1681 - ATATTTAAAGAAGGCAATAACAACTGTCCAATTCCTTTTTTATGTCAAAAAGACTATTCT - 1740
 561 -  I  F  K  E  G  N  N  N  C  P  I  P  F  L  C  Q  K  D  Y  S  -  580

1741 - GCTGCCATAAAGGACCAGGAAAGCACTGTAAATAAACGTTACAATACGGAATAAGTCC - 1800
 581 -  A  A  I  K  D  Q  E  S  T  V  N  K  R  Y  N  T  E  Y  K  S  -  600

1801 - AACAATCAGATAGCCCTCTTTTCCCAGCCTGACTGGGAAAGTCGTAAATTTAATTTCCGG - 1860
 601 -  N  N  Q  I  A  S  F  S  Q  P  D  W  E  S  R  K  F  N  F  R  -  620

1861 - AAATAAATTTAGAAAACGCAACCCTGAGTATAGGCCCGGATGCTAATGTAAAGGACAC - 1920
 621 -  K  L  N  L  E  N  A  T  L  S  I  G  R  D  A  N  V  K  G  H  -  640

1921 - ATAGAGGCTAAAAACTCTCAAATTGTTCTGGGAAATAAAACTGCATACATTGACATGTTC - 1980
 641 -  I  E  A  K  N  S  Q  I  V  L  G  N  K  T  A  Y  I  D  M  F  -  660

1981 - TCAGGAGAGAAAACATTACTGGCGAAGGTTTTGGATTCAGACAACAGCTTCGCTCCGGGGAT - 2040
 661 -  S  G  R  N  I  T  G  E  G  F  R  Q  Q  L  R  S  G  D  -  680

2041 - TCAGCAGGCCAAAGTAGTTTCAAGGGCAGTCTGAGTGCTCAAAAACAGCAAAATAACTGTT - 2100
 681 -  S  A  G  E  S  S  F  N  G  S  L  S  A  Q  N  S  K  I  T  V  -  700

2101 - GGTGATAAATCAACTGTTACTATGACTGGTGCATTATCCTTAATTAATACAGACCTGATT - 2160
 701 -  G  D  K  S  T  V  T  M  T  G  A  L  S  L  I  N  T  D  L  I  -  720
```

Fig. 13D
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
2161 - ATCAACAAAGGAGCTACTGTTACCGCCAGGGAAAAATGTATGTAGATAAAGCTATTGAA - 2220
 721 -  I  N  K  G  A  T  V  T  A  Q  G  K  M  Y  V  D  K  A  I  E  -  740

2221 - CTGGCCGGAACCCTGACATTAACAGGCACCCCTACAGAAAATAATAAATACAGCCCGGCA - 2280
 741 -  L  A  G  T  L  T  L  T  G  T  P  T  E  N  N  K  Y  S  P  A  -  760

2281 - ATCTATATGTCAGATGGATATAATATGACAGAAGATGGTGCCACGTTAAAGGCTCAAAAT - 2340
 761 -  I  Y  M  S  D  G  Y  N  M  T  E  D  G  A  T  L  K  A  Q  N  -  780

2341 - TATGCCTGGGTCAATGGTAATATAAAATCAGACAAAAAAGCATCTATTCTGTTTGGTGTT - 2400
 781 -  Y  A  W  V  N  G  N  I  K  S  D  K  K  A  S  I  L  F  G  V  -  800

2401 - GACCAGTATAAAGAAGATAACCTGGACAAAACCACACACCGCTGGCTACAGGTTTG - 2460
 801 -  D  Q  Y  K  E  D  N  L  D  K  T  T  H  T  P  L  A  T  G  L  -  820

2461 - CTGGGGTGGCTTTGATACTTCTTATACCGGAGGTATTGATGCTCCTGCAGCCTCAGCCAGC - 2520
 821 -  L  G  G  F  D  T  S  Y  T  G  G  I  D  A  P  A  A  S  A  S  -  840

2521 - ATGTATAACACCTTATGTGTTAGTAGAACATAGAGAATTCGGGTTCCATACTGACAGTAAAC - 2580
 841 -  M  Y  N  T  L  W  R  V  N  G  Q  S  A  L  Q  S  F  H  T  V  T  V  N  -  860

2581 - GACAGTCTTTTGTTGTTAGTAACATAGAGAATTCGGGTTCCATACTGTGACAGTAAAC - 2640
 861 -  D  S  L  L  F  S  N  I  E  N  S  G  F  H  T  V  T  V  N  -  880

2641 - ACACTGATGCCACTAATACTGCTGTGATTATGCGGGCTGATCTGAGCCAGTCTGTAAAT - 2700
 881 -  T  L  D  A  T  N  T  A  V  I  M  R  A  D  L  S  Q  S  V  N  -  900

2701 - CAATCGGATAAACTCATTGTTAAAAATCAGTTAACCGGAAGCAATAACAGTCTGTCGGTC - 2760
 901 -  Q  S  D  K  L  I  V  K  N  Q  L  T  G  S  N  N  S  L  S  V  -  920

2761 - GATATACAGAAAGTGGGAAATAATAACTTCAGGATTAACGTTGACCTGATAACAGCCCCA - 2820
 921 -  D  I  Q  K  V  G  N  N  S  G  L  N  V  D  L  I  T  A  P  -  940

2821 - AAAGGAAGCAATAAAGAGATATTTAAAGCCAGTACTCAGGCCATAGGTTTCACCAACATA - 2880
 941 -  K  G  S  N  K  E  I  F  K  A  S  T  Q  A  I  G  F  S  N  I  -  960

2881 - TCTCCTGTGATCAGCACCAAAGAGGATCAGGAACATACCACTGACCCTGACCGGATAT - 2940
 961 -  S  P  V  I  S  T  K  E  D  Q  E  H  T  T  W  T  L  T  G  Y  -  980

2941 - AAGTGGCTGAAAATACACGCATCTTCCGGTGCAGCAAAATCGTATATGTCCGGTAATTAC - 3000
 981 -  K  V  A  E  N  T  A  S  S  G  A  A  K  S  Y  M  S  G  N  Y  - 1000
```

Fig. 13E
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
3001 - AAAGCCTTCCTGACAGAAGTCAACAACCTGAATAAACGAATGGGGATCTGCGTGACACC  - 3060
1001 -  K   A   F   L   T   E   V   N   N   L   N   K   R   M   G   D   L   R   D   T  - 1020

3061 - AATGGCGAGGCCGGTGCATGGGCCCGCATCATGAGCGGAGCAGTTCAGCTTCTGTGGA    - 3120
1021 -  N   G   E   A   G   A   W   A   R   I   M   S   G   A   G   S   A   S   G   G  - 1040

3121 - TACAGTGACAACTACACCCATGTGCAGATTGGTCTGACATAAAAAACATGAGCTGGATGGA - 3180
1041 -  Y   S   D   N   Y   T   H   V   Q   I   G   V   D   K   K   H   E   L   D   G  - 1060

3181 - CTTGACCTTTTTCACTGGTCTGACTATGACGGTATACCGACAGTCATGCCAGCAGTAATGCA - 3240
1061 -  L   D   L   F   T   G   L   T   M   T   Y   T   D   S   H   A   S   S   N   A  - 1080

3241 - TTCAGTGGCAAGACGAAGTCCGTCGGGGCAGGTCTGTATGCTTCCGCTATATTTGACTCT  - 3300
1081 -  F   S   G   K   T   K   S   V   G   A   G   L   Y   A   S   A   I   F   D   S  - 1100

3301 - GGTGCCTATATCGACCTGATTAGTAAGTATGTTCACCATGATAATGAGTACTCGGCGACC - 3360
1101 -  G   A   Y   I   D   L   I   S   K   Y   V   H   H   D   N   E   Y   S   A   T  - 1120

3361 - TTTGCTGGACTCGGAACAAAAGACTACAGTTCTCATTCCTTGTATGTGGGTGCTGAAGCA - 3420
1121 -  F   A   G   L   G   T   K   D   Y   S   S   H   S   L   Y   V   V   G   A   E   A - 1140

3421 - GGCTACCGCTATCATGTAACAGAAGACTCCTGGATTGAGCCGCAGGCAGAACTGGTTTAT - 3480
1141 -  G   Y   R   Y   H   V   T   E   D   S   W   I   E   P   Q   A   E   L   V   Y  - 1160

3481 - GGGGCCGTATCAGGTAAACGGTTCGACTGGCAGGATCGCGGAATGAGCGTGACCATGAAG - 3540
1161 -  G   A   V   S   G   K   R   F   D   W   Q   D   R   G   M   S   V   T   M   K  - 1180

3541 - GATAAGGACTTTAATCCGCTGATTGGGCGTACCGGTGTTGATGTGGGTAAATCCTTCTCC - 3600
1181 -  D   K   D   F   N   P   L   I   G   R   T   G   V   D   V   G   K   S   F   S  - 1200

3601 - GGTAAGGACTGGAAAGTCACAGCCCGCGCCGGTTTGGCTACCAGTTTGACCTGTTTGCC   - 3660
1201 -  G   K   D   W   K   V   T   A   R   A   G   L   G   Y   Q   F   D   L   F   A  - 1220

3661 - AACGGTGAAACCGTACTGCGTGATGCGTCCGGTGAGAAACGTATCAAAGGTGAAAAGAC  - 3720
1221 -  N   G   E   T   V   L   R   D   A   S   G   E   K   R   I   K   G   E   K   D  - 1240

3721 - GGTCGTATTCTCATGAATGTTGGTCTCAACGGCGATAATCTTCGCTTCGGT          - 3780
1241 -  G   R   I   L   M   N   V   G   L   N   A   E   I   R   D   N   L   R   F   G  - 1260

3781 - CTTGAGTTTGAGAAATGAGCATTGGTAAATACACGTGGATAACGCGATCAACGCCAAC   - 3840
```

Fig. 13F
SigA fragment sequence: the sequence of full length SigA protein is depicted. The nucleotide sequence (SEQ ID NO:3) and corresponding amino acid sequence (SEQ ID NO:4) of the SigA2 portion are indicated in the boxed region.

```
1261 - L  E  F  F  E  K  S  A  F  G  K  Y  N  V  D  N  A  I  N  A  N  - 1280
3841 - TTCCGTTACTCTTTCTGA  - 3858
1281 - F  R  Y  S  F  *  - 1300
```

SHIGELLA PROTEIN ANTIGENS AND METHODS

CROSS-REFERENCE TO PRIOR APPLICATIONS

This application is a divisional of U.S. application Ser. No. 12/603,574, filed Oct. 21, 2009, which claims priority pursuant to 35 U.S.C. §119 to U.S. Provisional Patent Application No. 61/107,306, filed Oct. 21, 2008, both of which are hereby incorporated by reference in their entirety.

FIELD OF THE INVENTION

The present invention relates to novel protein antigens of *Shigella* spp., and also present on *Escherichia coli* enteroinvasive strains and methods for use of these antigens for developing vaccines against shigellosis caused by *Shigella* species and serotypes, and against disease caused by enteroinvasive *E. coli* (EIEC) bacteria. The invention also relates to use of the novel antigens and corresponding antibodies for diagnosis of shigellosis and for identification of *Shigella* bacteria.

BACKGROUND OF THE INVENTION

*Shigella* spp. is a Gram-negative bacterial pathogen that causes bacillary dysentery in humans by infecting epithelial cells of the colon. *Shigella* primarily infects intestinal epithelial cells (IECs). *Shigella* expresses several proteins that provide a mechanism for delivering effectors that induce bacterial uptake into the host cell via phagocytosis. To accomplish the injection of the effectors, *Shigella* use a type III secretion (TTS) system to induce their entry into epithelial cells and to trigger apoptosis in infected macrophages.

Bacteria of *Shigella* spp., including *S. dysenteriae*, *S. flexneri*, *S. boydii* and *S. sonnei*, are responsible for shigellosis in humans, a disease characterized by the destruction of the colonic epithelium that is responsible for 1 million deaths per year, mostly children in developing countries.

There are 15 serotypes in *S. dysenteriae*, 14 serotypes and subtypes are recognized in *S. flexneri*, *S. boydii* has 20 serotypes and a single serotype exist within *S. sonnei* although their prevalence is not evenly distributed. The most prevalent *Shigella* spp. in industrialized countries and of increasing prevalence in some Latin American countries is *S. sonnei*. *S. dysenteriae* type 1, which can produce Shiga-toxin, can cause high morbidity and mortality. *S. flexneri* is most prevalent in endemic region of developing countries. The World Health Organization (WHO) considered the development of a vaccine against shigellosis a priority for developing countries.

Although control and treatment of shigellosis outbreaks with antibiotics is possible, the high cost of antibiotics and the constant emergence of antibiotic resistant *Shigella* species, even to the newest antibiotics, underscores the need for an effective vaccine to help control *Shigella* and related enteroinvasive *E. coli* diseases in the developing regions of the world (12).

To establish a successful infection, *Shigella* finely regulates the host's immune response, especially those responses leading to inflammation. In contrast to *Salmonella typhimurium*, *Shigella* is inefficient at invading the apical pole of polarized intestinal epithelial cells. Instead, *Shigella* requires transmigration of polymorphonuclear leucocytes (PMN) to disrupt the epithelial barrier, facilitating cell invasion via the basolateral pole of epithelial cells (26). The host's inflammatory response, facilitated by cells of the innate immune system, attracts PMN to the site of inflammation. Therefore, triggering inflammation at the early stage of infection is required for cell invasion by *Shigella*. Bacteria that reach the intracellular compartment of the cells grow and spread from cell to cell, protected from host immune defenses. But, infected epithelial cells playa large role in the inflammatory process, both as sentinels that detect bacterial invasion and as a major source of mediators, particularly cytokines and chemokines that initiate and orchestrate mucosal inflammation. Recognition of the bacteria by the epithelial cells occurs essentially intracellularly via a cytoplasmic molecule, Nod1/CARD4 that senses a microbial motif, the peptidoglycan (8). Nod1 activation induces other proinflammatory signaling pathways including NF-κ3 and c-Jun N-terminal kinase (JNK) that lead to the expression of chemokines, such as interleukin 8 (IL-8). Thus triggering excessive inflammation is detrimental to *Shigella*'s survival in the host.

Natural *Shigella* infections confer immunity and provide protection against subsequent infection with homologous virulent *Shigella* (5). This exclusively human disease is transmitted directly via the fecal-oral route from an infected patient or indirectly through contaminated food and water. It is a highly contagious infection, capable of transmission with as few as 100 microorganisms (6). Epidemiologic and volunteer studies have revealed that protective immunity against *Shigella* is directed against the LPS or O-specific antigen and is therefore related to serotype. Many approaches have been used for *Shigella* vaccines including use of live attenuated *Shigella* (16, 22), killed *Shigella* whole bacteria (18), and *Shigella* lipopolyssacharide (LPS) or O-polysaccharides conjugated to carriers such as proteosomes (24), tetanus toxoid (25) and ribosomes (31). Despite many years of extensive research, an effective and inexpensive vaccine against these *Shigella* species is not yet available.

The use of attenuated strains of *Shigella* as live oral vaccines has been demonstrated to induce protective efficacy. Results from the clinical trials of genetically well characterized, invasive *Shigella* vaccines are promising. CVD1208, SC602, WRSS1 add WRSd1 vaccine candidates, administered orally, are safe and immunogenic in volunteer trials and, in the case of SC602, have been demonstrated to protect against dysentery (11, 16, 17, 33). Clinical trials with CVD1208 demonstrated that the symptoms of mild fever and diarrhea, which are seen with some of the live *Shigella* vaccines, can be reduced by elimination of the sen and set genes from the vaccine strain. Duplication of a successful strategy in one serotype to other serotypes is an ongoing area of research but will eventually require use of a polyvalent mixture of *Shigella* strains of different serotypes that can protect against most of the *Shigella* (21). A recent multi centre study of *Shigella* diarrhoea in six Asian countries indicated that the relative distribution of *Shigella* species isolated from patients varied from different countries and sites. Moreover, *S. flexneri* serotypes were highly heterogeneous in their distribution from site to site, and even from year to year. The heterogeneous distribution of *Shigella* species and serotypes suggest that multivalent or cross-protective *Shigella* vaccines will be needed to prevent shigellosis worldwide (35). A vaccine that aims to confer broad-spectrum coverage would require inclusion of all of the important *Shigella* serotypes (21). To resolve this dilemma a vaccine strategy based on the use of 'pentavalent formulations', comprising *S. flexneri* 2a, 3a and 6 strains along with the attenuated *S. sonnei* and *S. dysenteriae* 1 strains has been advocated (Noriega et al., 1994). Alternatively, use of complex structures comprised of serotype-specific and cross-reactive antigens from *Shigella*, such as whole bacteria either killed or live-attenuated, could be considered as an approach to vaccinate against infections caused by the most common species and serotypes of *Shigella*. Intranasally administered Invaplex, a purified complex from *Shigella* water extract composed of the Ipa proteins and LPS, has been proposed and is in Phase 1 trials currently at the Walter Reed Army Institute of Research (WRAIR) (23).

There is thus a need for an effective vaccine to help control *Shigella* and related enteroinvasive *E. coli* diseases in the developing regions of the world.

SUMMARY OF THE INVENTION

In certain embodiments, the invention relates to a vaccine composition for immunizing a mammal against *Shigella* comprising an amount of a *Shigella* protein from the group consisting of IcsP2 and SigA2 proteins effective to elicit an immune response against *Shigella*, and a pharmaceutically acceptable carrier or diluent. In certain embodiments, the *Shigella* IcsP2 and SigA2 proteins are chemically conjugated or genetically fused with other proteins.

In additional embodiments, the invention relates to a vaccine composition for immunizing a mammal against *Shigella* comprising an amount of *Shigella* IcsP2 effective to elicit an immune response against *Shigella*, and a pharmaceutically acceptable carrier or diluent.

In yet additional embodiments, the invention relates to a vaccine composition for immunizing a mammal against *Shigella* comprising an amount of *Shigella* SigA2 effective to elicit an immune response against *Shigella*, and a pharmaceutically acceptable carrier or diluent.

In yet additional embodiments, the invention relates to a vaccine composition for immunizing a mammal against *Shigella* comprising an amount of chemically conjugated or genetically fused IcsP2 and SigA2.

In certain embodiments, the vaccine composition further comprises an adjuvant.

In certain embodiments, the adjuvant is an oil phase of an emulsion selected from a group consisting of a water-in-oil emulsion and a double oil emulsion.

In additional embodiments, the invention relates to an isolated polypeptide comprising an amino acid sequence as set forth in SEQ ID NO:2 (for *Shigella* IcsP2).

In additional embodiments, the invention relates to an isolated polypeptide comprising an amino acid sequence as set forth in SEQ ID NO: 4 (for SigA2).

In additional embodiments, the invention relates to a an isolated nucleic acid sequence encoding the *Shigella* IcsP2 polypeptide.

In additional embodiments, the invention relates to an isolated nucleic acid sequence encoding the SigA2 polypeptide.

In additional embodiments, the invention relates to an isolated nucleic acid sequence encoding the *Shigella* IcsP2 polypeptide and the SigA2 polypeptide.

In additional embodiments, the invention relates to a vector comprising the nucleic acid sequence encoding the *Shigella* IcsP2 polypeptide or the SigA2 polypeptide. In additional embodiments, the invention relates to a host cell transfected with any of the vectors described herein.

In additional embodiments, the invention relates to a method for producing *Shigella* IcsP2 and SigA2 polypeptides comprising culturing any of the host cells described herein under suitable conditions for protein expression and collecting said polypeptides from the cultured cells.

In additional embodiments, the invention relates to an immunogenic composition comprising a) *Shigella* IcsP2 and SigA2, and b) an adjuvant, wherein the amounts of a) and b) in combination are effective to elicit an immune response against *Shigella*.

In additional embodiments, the invention relates to a method of treating a mammal suffering from or susceptible to a pathogenic infection, comprising administering an effective amount of the vaccine composition described herein. In certain embodiments, the effective amount of the vaccine composition ranges between about 10 micrograms to about 2 milligrams In additional embodiments, the invention relates to a method for modulating the immune response of a mammal comprising administering an effective amount of any one of the vaccine compositions described herein. In certain embodiments, the effective amount of the vaccine composition is from about 10 micrograms to about 2 milligrams.

In additional embodiments, the invention relates to an antibody that specifically binds to the *Shigella* IcsP2 polypeptide.

In additional embodiments, the invention relates to an antibody that specifically binds to the SigA2 polypeptide. In certain embodiments, the antibody further comprises a label. In additional embodiments, the label is selected from the group consisting of an enzyme, protein, peptide, antigen, antibody, lectin, carbohydrate, biotin, avidin, radioisotope, toxin and heavy metal. In additional embodiments, the antibody is a humanized antibody. In additional embodiments, the antibody is a CDR-grafted antibody. In additional embodiments, the antibody is a chimeric antibody. In additional embodiments, the antibody is an antibody fragment. In additional embodiments, the antibody is a monoclonal antibody. In additional embodiments, the antibody is a polyclonal antibody.

In additional embodiments, the invention relates to a conjugate molecule comprising a saccharide comprising an O antigen of *Shigella* bacteria covalently bound to a *Shigella* IcsP2 or SigA2 protein.

In additional embodiments, the invention relates to a conjugate molecule comprising a saccharide comprising an O antigen of *Shigella* bacteria covalently bound to a polypeptide as described herein.

In additional embodiments, the invention relates to a vaccine comprising a conjugate molecule as described herein for immunizing a mammal against shigellosis.

In additional embodiments, the invention relates to a conjugate molecule comprising a saccharide from a bacteria non related to the genus *Shigella*, said saccharide being covalently bound to a *Shigella* IcsP2 or SigA2 protein.

In additional embodiments, the invention relates to a conjugate molecule comprising a saccharide from a bacteria non related to the genus *Shigella*, said saccharide being covalently bound to a polypeptide as described herein.

In additional embodiments, the invention relates to a vaccine comprising a conjugate molecule as described herein for immunizing a mammal against shigellosis and typhoid disease.

BRIEF DESCRIPTION OF THE DRAWINGS

FIG. 9 shows test antisera to SigA2 inhibited plaque formation induced by *S. flexneri*. The number of plaques induced by invasive *S. flexneri* 2a in infected cells was reduced in the presence of mouse antiserum to SigA2 (FIG. 9B) compared to the negative control, i.e., without antiserum (FIG. 9A).

FIGS. 11A-D show that antibodies against SigA2 inhibited keratoconjunctivitis by *S. flexneri* 2a.

FIG. 12 shows the DNA sequence of the IcsP2 fragment and its position within the sequence of full-length IcsP. The IcsP2 fragment was extracted from the full-length iscP gene of the whole genomic sequence of strain *S. flexneri* 2a 2457T.

FIG. 13 shows the DNA sequence of the SigA2 fragment and its position within the sequence of full-length SigA. The SigA2 fragment was extracted from the full-length sigA gene of the whole genomic sequence of strain *S. flexneri* 2a 2457T.

DETAILED DESCRIPTION

Figure 1:
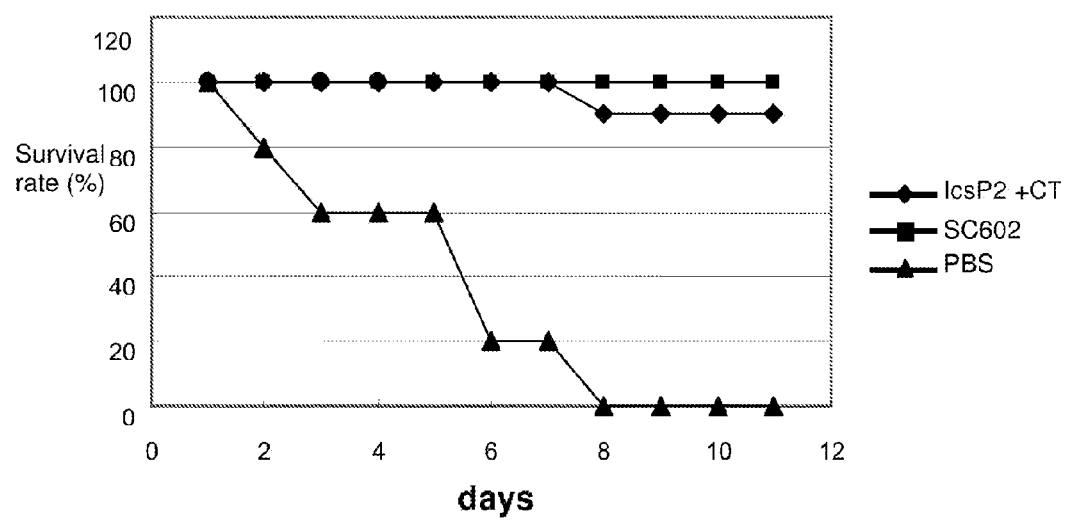
FIG. 1 shows that immunization with IcsP2 protein and CT (IcsP2+CT) protected animals against lung challenge with *S. flexneri* 2a. The results also show that intranasal administration of a live-attenuated *S. flexneri* vaccine strain (SC602) protected mice against challenge.

The present invention relates to the identification of IcsP and SigA as candidate protein antigens in the composition of vaccines against *Shigella* infections. More specifically, the present invention relates to specific polypeptide moieties or fragments of *Shigella* IcsP and SigA, capable of inducing protective immune responses against infection caused by virulent *Shigella* bacteria. Said specific polypeptides are referred to hereafter to as IcsP2 and SigA2, respectively. IcsP2 is common to all *Shigella* spp. and is also present on EIEC. SigA2 is present on strains of *S. flexneri* 2a and of *S. boydii* and *S. sonnei.*

The present invention relates to protein antigens IcsP and SigA identified as surface-associated and/or secreted from *Shigella* that are common to *Shigella* types and species including *S. flexneri, S. sonnei, S. boydii* and *S. dysenteriae* and which can protect against shigellosis and other enteric infections when administered as vaccines. In addition, the present invention relates to certain of such antigens that are also common between *Shigella* species and EIEC. The invention also relates to the use of antibodies raised against these antigens and of DNA probes for use in the diagnosis of *Shigella* and EIEC infections.

Antigen Identification and Characteristics of the Antigens

The whole genome sequences of *Shigella* spp., *S. flexneri* 2a strains 2457T (37) and Sf301 (15), *S. flexneri* 5b strain Sf8401 (20), *s. dysenteriae* 1, strain Sd197, *S. boydii* serotype 4, strain Sb227 and *S. sonnei* strain Ss046 are available (38, 39). Besides the whole genome sequences of those *Shigella* strains, the complete nucleotide sequences of the virulence plasmid from a number of *Shigella* spp. are also available (3, 14).

IcsP

*Shigella* movement within the host cell cytoplasm is dependent on the ability of the bacterium to recruit host cell actin to its surface to form an actin tail, which propels the bacterium from one cell to another (2). Actin tail assembly is mediated by a single bacterial protein IcsA, which is found on the outer surface at one pole of the bacterium, that pole at which actin assembly occurs (27). The IcsA protein is localized to the old pole of the bacterium and is both necessary and sufficient for actin assembly (9). The icsA gene is located on the *Shigella* virulence plasmid, and since it is essential for the movement of the bacteria, it is present among all the serotypes and species (38). The IcsA protein is comprised of two domains: the α-domain (residues 53 to 758) contains the determinant for actin assembly and extends from the bacterial surface into the extracellular environment, whereas the β-domain (residues 759 to 1102) is embedded in the outer membrane (32).

IcsA is slowly cleaved from the bacterial surface by the outer membrane protease IcsP (7). IcsP is encoded by a monocistronic operon on the large (230-kb) virulence plasmid of *Shigella* (3). Absence of IcsP leads to an alteration in the distribution of surface IcsA, such that the polar cap is maintained and some IcsA is distributed along the lateral walls of the bacterium. The amino acid sequence of 327 a.a polypeptide has 58% sequence identity to each of *E. coli* proteases OmpP and OmpT, 42% sequence identity to the *Salmonella typhimurium* protease E precursor, PrtA and 40% sequence identity to the *Yersinia pestis* fibrinolysin precursor Pla (29).

SigA

The sigA gene is situated on the pathogenicity island of *Shigella flexneri* 2a chromosomal DNA. Although sigA was believed to be exclusively found in serotype 2a of *S. flexneri*, the presence of sigA has also been reported in *S. boydii* and *S. sonnei* (38). Sequence analysis indicates that sigA encodes a 139 kDa protein which belongs to the SPATE (serine protease autotransporters of Enterobacteriaceae) subfamily of autotransporter proteins (1). Amino acid identity of SigA protein as compared to enteroaggregative *E. coli* autotransporter Pet, an enterotoxic and cytopathic protease, is 58% (1). SigA mutant bacteria shows reduced fluid accumulation as compared to the wild type *Shigella*, however, the mutant bacteria still is capable of inducing substantial fluid accumulation, which implies that SigA is only one of a number of enterotoxins produced by *S. flexneri* 2a.

Identification of novel antigens common to most, if not all, species and serotypes of *Shigella* would be ideal provided that such antigens are indeed protective. Genomics and proteomics have had a dramatic effect on the ability to find new vaccine targets and develop effective vaccines and some *Shigella* surface proteins are recognized as possible vaccine candidates for Shigellosis (13, 19, 36).

The present invention also relates to the cloning, expression and purification of *Shigella* proteins of interest. The purified proteins were used to immunize and evaluate protective immunity in three animal models 1) mouse pneumonia model, 2) guinea pig keratoconjunctivitis model, and 3) guinea pig colitis model (such models are described in 10, 28, 30).

In certain embodiments, the invention provides methods for screening common protein antigens of *Shigella* spp and the methods used in this invention may be applied to screening of protein antigens of mucosal pathogens.

In certain embodiments, the invention provides methods for producing specific antibodies to said *Shigella* IcsP2 and SigA2 polypeptides and for preparing corresponding DNA probes specific for said common antigens. Such antibodies and DNA probes can be used for detection of bacteria expressing said common antigens or corresponding genes, for the diagnosis of bacillary dysentery caused by *Shigella* and EIEC. Therapeutic antibodies can also be used to treat patients suffering from acute bacillary dysentery caused by bacteria expressing the corresponding protein antigens.

Diagnosis of Bacillary Dysentery

Aside from *Shigella* ssp, certain strains of *Escherichia coli* can cause dysentery. Currently, there are four recognized classes of enterovirulent *E. coli* (collectively referred to as the EEC group) that cause gastroenteritis in humans. *E. coli* is part of the normal intestinal flora of humans and other primates. A minority of *E. coli* strains are capable of causing human illness by several different mechanisms. Among these are the enteroinvasive (EIEC) strains. It is unknown what foods may harbor these pathogenic enteroinvasive (EIEC) strains responsible for a form of bacillary dysentery. Enteroinvasive *E. coli* (EIEC) may produce an illness known as bacillary dysentery. The EIEC strains responsible for this syndrome are closely related to *Shigella* ssp. Following the ingestion of EIEC, the organisms invade the epithelial cells of the intestine, resulting in a mild form of dysentery, often mistaken for dysentery caused by *Shigella* species. The illness is characterized by the appearance of blood and mucus in the stools of infected individuals. The diagnosis of *Shigella* and EIEC infection is relatively difficult since the bacteria must be isolated from stools and the infectious dose of *Shigella* and EIEC is thought to be as few as 10 to 100 organisms.

The culturing of the organism from the stools of infected individuals and the demonstration of invasiveness of isolates in tissue culture or in a suitable animal model is necessary to diagnose dysentery caused by this organism. However, such an approach is cumbersome and time-consuming.

Echeverria P. et al. describe that "( . . . ) the four *Shigella* species (*S. dysenteriae, S. flexneri, S. boydii,* and *S. sonnei*) are classically identified by culture of fecal specimens on selective media and testing of isolates for agglutination by species-specific antisera. DNA probes have been used to identify both lactose-fermenting and non-lactose-fermenting EIEC as well as *Shigella* isolates that do not agglutinate in antisera. These DNA probes are not necessary for the identification of *Shigella* if a competent bacteriology laboratory with *Shigella* antisera is available. The clinical illness associated with EIEC infections is similar to shigellosis. Fewer children with EIEC infections than with shigellosis, however, have occult blood in stool (36% vs. 82%) and more than 10 fecal leukocytes per high-power field (36% vs. 67%). Standard bacteriologic methods and testing of *E. coli* isolates for hybridization with the *Shigella*/EIEC probe are currently the most sensitive means of diagnosing infections caused by these enteric pathogens. A more rapid method of identifying *Shigella* and EIEC infections in a situation where a bacteriology laboratory is not available involves immunological assays" (40), Rev. Infect. Dis. 1991 March-April; 13 Supp 14:S220-5).

The present invention relates in part to the finding that IcsP2 is also expressed by EIEC and its sequence is highly homologous to that of *Shigella* IcsP2, but not to genes of the other 3 classes of enterovirulent *E. coli* (EEC). Consequently, an aspect of the present invention relates to IcsP2 as a protective agent against EIEC as well as DNA probes and specific antibodies to *Shigella* IcsP2 that can be used to diagnose dysentery caused by both *Shigella* and EIEC.

In one embodiment, the *Shigella* polypeptide antigens disclosed in the present invention are administered with a pharmaceutically acceptable diluent. Such formulations can be administered by an injection (subcutaneous, intradermal, intramuscular) or applied topically onto the skin using an adhesive patch. Alternatively, the vaccine is administered by a mucosal route (oral, buccal, sublingual, nasal drops, aerosol, rectal) using a pharmaceutically acceptable vehicle. The antigens can also be mixed with an adjuvant to enhance the ensuing immune responses. Example of such adjuvants are without being limited to, aluminium salts, ISCOMs, saponin-based adjuvants, oil-in-water and water-in-oil emulsions, toll-like receptor ligands such as muramyl dipeptide, *E. coli* LPS, oligonucleotides comprised of unmethylated DNA, poly I:C, lipoteichoic acid, peptidoglycan. Enterotoxins and their adjuvant active derivatives such as cholera toxin, heat-labile *E. coli* enterotoxin, pertussis toxin, shiga toxin and analogs.

In a further embodiment of the invention the antigens disclosed are cloned and expressed in non virulent or in an attenuated bacteria and the later are used as vectors containing a DNA promoter element capable of initiating the synthesis of mRNA operably linked to an open reading frame containing one or both of the genes encoding *Shigella* IcsP and SigA. The resultant protein(s) is(are) exported and assembled on the bacterial surface and/or periplasm. Such non virulent or attenuated bacteria can then be used as oral or mucosal vaccine. Examples of bacterial vectors are known in the art, such as *E. coli, Salmonella* spp., *Shigella* spp., *Vibrio cholera, Bacillus spp, Clostridium* spp, *Listerium monocytogenes, Mycobacterium* spp., *Lactobacillus* spp., *Lactococcus* spp., *Streptococcus gordonii*. In another embodiment, the IcsP and the SigA antigens are being overexpressed in non virulent strains or mutant strains of *Shigella* that have been equipped with a suitable promoter. Such bacteria expressing either IcsP or SigA antigens or both can then be used as live vaccines against shigellosis. Alternatively, such overexpressing strains can be inactivated with formalin or by heating and the resulting bacteria can be used as killed vaccines. Further embodiments of the invention are vectors used to transform *Shigella* species which results in the periplasmic expression of heterologous antigens. This expression is not likely to alter either *Shigella*'s natural tissue tropism (colonic epithelium) following oral administration or significantly reduce strain invasiveness. Suitable *Shigella* species include live, attenuated vaccine strains of *S. sonnei, S. dysenteriae, S. flexneri*, and *S. boydii*. Exemplified transformed *Shigella* strains include *Shigella* vaccine strain, e.g. *Shigella flexneri* 2a (SC608 (3098)), *Shigella flexneri* 2a (SC608 (cfaAE)), *Shigella flexneri* 2a (SC608 (pCFAI)) and *Shigella flexneri* 2a (SC608 (pCFAI/LTB)). These strains are characterized as having deletions in icsA, a gene that enables intracellular and intercellular spread of *Shigella* in host epithelial cells and in the gene iucA that plays a role in iron acquisition by the bacteria. These transformed *Shigella* strains are suitable for use in immunogenic composition, in particular oral or mucosally administered vaccines. Other bacteria have been described and are well known in the art for use as vector systems:

- *Salmonella* and *E. coli* bacterial surface proteins have been used as carriers or vehicles of foreign epitopes for various purposes, including the development of live vaccines (U.S. Pat. No. 5,348,867, Inventors Georgiou, George, Francisco, Joseph A, Earhart, Charles F.)
- *Lactobacillus* harboring an expression cassette encoding a signal sequence, wherein the biologically active polypeptide is linked to a heterologous carboxy-terminal target region. (WO/2005/012491, PCT/US2004/002460) Inventors: CHANG, Chia-Hwa, L1U, Xiaowen et al.)

Bacterial surface protein expression: Smit, John; and, Nina Agabian; "Cloning of the Major Protein of the *Coulobacter crescentus* Periodic Surface Layer: Detection and Characterization of the Cloned Peptide by Protein Expression Assays" (1984) J. Bacteriol. 160, 1137-1145. U.S. Pat. No. 5,500,353.

Compartmentalization of recombinant polypeptides in host cells. (PCT/EP00/00686, U.S. Pat. No. 6,610,517, Inventor Werner Lubitz).

Yeast cell surface display of proteins and uses thereof (U.S. Pat. No. 6,423,538) Wittrup, K. Dane et al.).

Recombinant mycobacteria, particularly recombinant *M. bovis* BCG, which express heterologous DNA encoding a product (protein or polypeptide) of interest (U.S. Pat. No. 5,591,632) O'Donnell, Michael A. et al.)

Use of gram-positive bacteria to express recombinant proteins (U.S. Pat. No. 5,821,088) Darzins, Aldis et al. Gianni Pozzi et al., "Delivery and Expression of a Heterologous Antigen on the Surface of Streptococci", Infection and Immunity (May 1992) 60:1902-1907

Method for expression and secretion in *bacillus* (U.S. Pat. No. 5,032,510)—S. Kovacevic et al.

The vectors that are used to introduce IcsP and/or SigA polypeptides into mammalian cells, tissues, organs or organisms also comprise attenuated viruses equipped with a suitable promoter element that control expression of the trans genes encoding IcsP and/or SigA can be prepared and used to produce IcsP and/or SigA. Examples of viral vectors that can be used to express IcsP and/or SigA include without being limited to adenoviruses, polioviruses, a sindbis virus vector, Semliki Forrest virus, a poxvirus, a papilloma virus, a retrovirus or a lentivirus. Additional vectors used to express IcsP and/or SigA include virus-like particles (VLP) and bacteriophages.

Additionally, IcsP and SigA can be incorporated into a recombinant expression vector comprising a selection gene, a yeast sequence, and a polynucleotide encoding IcsP and/or SigA, wherein said polynucleotide is operably linked to a yeast promoter and said vector is being used to transfect yeast cells which produce IcsP and/or SigA polypeptides of the present invention. The recombinant expression vectors of the invention can be designed for expression of the proteins of the invention in yeast cells. Methods of expressing proteins in yeast, such as *Saccharomyces cerevisiae, Pichia pastoris, Hansenula polymorpha*, and *Kluyveromyces lactis*, are well-known in the art.

The present invention also relates to the use of reagents specific for the IcsP and SigA genes and the IcsP2 and SigA2 polypeptides in the design of diagnostic tests.

In a further embodiment of the invention the antigens disclosed are cloned and expressed in non virulent or in an attenuated bacteria and the later are used as vectors containing a DNA promoter element capable of initiating the synthesis of mRNA operably linked to an open reading frame containing one or both of the genes encoding *Shigella* IcsP and SigA. The resultant protein(s) is(are) exported and assembled on the bacterial surface and/or periplasm. Such non virulent or attenuated bacteria can then be used as oral or mucosal vaccine. In another embodiment, the IcsP and the SigA antigens are being overexpressed in non virulent strains or mutant strains of *Shigella* that have been equipped with a suitable promoter. Such bacteria expressing either IcsP or SigA antigens or both can then be used as live vaccines against shigellosis. Alternatively, such overexpressing strains can be inactivated with formalin or by heating and the resulting bacteria can be used as killed vaccines. Further embodiments of the invention are vectors used to transform *Shigella* species which results in the periplasmic expression of heterologous antigens. This expression is not likely to alter either *Shigella*'s natural tissue tropism (colonic epithelium) following oral administration or significantly reduce strain invasiveness. Suitable *Shigella* species include live, attenuated vaccine strains of *S. sonnei, S. dysenteriae, S. flexneri*, and *S. boydii*. Exemplified transformed *Shigella* strains include *Shigella* vaccine strain, e.g. *Shigella flexneri* 2a (SC608 (3098)), *Shigella flexneri* 2a (SC608 (cfaAE)), *Shigella flexneri* 2a (SC608 (pCFAI)) and *Shigella flexneri* 2a (SC608 (pCFAI/LTB)). These strains are characterized as having deletions in icsA, a gene that enables intracellular and intercellular spread of *Shigella* in host epithelial cells and in the gene iucA that plays a role in iron acquisition by the bacteria. These transformed *Shigella* strains are suitable for use in immunogenic composition, in particular oral or mucosally administered vaccines. Other bacteria have been described and are well known in the art for use as vector systems:

*Salmonella* and *E. coli* bacterial surface proteins have been used as carriers or vehicles of foreign epitopes for various purposes, including the development of live vaccines (U.S. Pat. No. 5,348,867, Inventors Georgiou, George, Francisco, Joseph A, Earhart, Charles F.)

*Lactobacillus* harboring an expression cassette encoding a signal sequence, wherein the biologically active polypeptide is linked to a heterologous carboxy-terminal target region. (WO/2005/012491, PCT/US2004/002460) Inventors: CHANG, Chia-Hwa, L I U, Xiao-wen et al.)

Bacterial surface protein expression: Smit, John; and, Nina Agabian; "Cloning of the Major Protein of the *Caulobacter crescentus* Periodic Surface Layer: Detection and Characterization of the Cloned Peptide by Protein Expression Assays" (1984) J. Bacteriol. 160, 1137-1145. U.S. Pat. No. 5,500,353.

Compartmentalization of recombinant polypeptides in host cells. (PCT/EP00/00686, U.S. Pat. No. 6,610,517, Inventor Werner Lubitz).

Yeast cell surface display of proteins and uses thereof (U.S. Pat. No. 6,423,538) Wittrup, K. Dane et al.).

Recombinant mycobacteria, particularly recombinant *M. bovis* BCG, which express heterologous DNA encoding a product (protein or polypeptide) of interest (U.S. Pat. No. 5,591,632) O'Donnell, Michael A. et al.)

Use of gram-positive bacteria to express recombinant proteins (U.S. Pat. No. 5,821,088) Darzins, Aldis et al. Gianni Pozzi et al., "Delivery and Expression of a Heterologous Antigen on the Surface of Streptococci", Infection and Immunity (May 1992) 60:1902-1907

Method for expression and secretion in *bacillus* (U.S. Pat. No. 5,032,510)—S. Kovacevic et al.

The present invention also relates to the use of reagents specific for the IcsP and SigA genes and the IcsP2 and SigA2 polypeptides in the design of diagnostic tests.

The technique of gene amplification referred to as polymerase chain reaction (PCR) is well known in the art and has been used for the diagnosis of *Shigella* infections (41). The present invention discloses specific primers capable of binding to the IcsP2 and the SigA2 gene sequences. Such primers can be used to amplify either icsP or sigA genes from bacteria present in a clinical sample (e.g. stool) and the amplified fragment can be detected by visual, photometric, isotopic or fluorometric methods. Thus, the present invention claims the use of oligonucleotide primers specific for said IcsP2 and SigA2 gene sequences in the diagnosis of dysentery caused by *Shigella* spp and EIEC.

The present invention also relates to the production of antisera against SigA2 and IcsP2. Such antisera were capable of reacting with corresponding polypeptides expressed by different species of *Shigella*. Further, such antisera were capable of inhibiting in vitro infection of HeLa cells by *Shigella* bacteria and of protecting animals against inflammation caused by *Shigella*, in a keratoconjunctivitis model.

The present invention also relates to conjugates of IscP2 and an O polysaccharide antigen of *Shigella* and conjugates of the SigA2 and of O polysaccharide antigen of *Shigella*. The O-specific polysaccharides on the surface of pathogenic bacteria are thought to be both protective antigens and essential virulence factors. The inability of most polysaccharides to elicit protective levels of anti-polysaccharide antibodies in infants and adults with weakened immune systems could be overcome by their covalent attachment to proteins that conferred T-cell dependent properties. This principle led to the construction of vaccines against *Haemophilus influenzae* b (Hib), pneumococcal pneumonia, and *Neisseria meningitidis*. Extension of the conjugate technology to the O-specific polysaccharides of Gram-negative bacteria provided a new generation of glycoconjugate vaccines. Originally, Avery and Goebel in J. Exp. Med. 50:531 (1929) and Goebel in J. Exp. Med. 50:469-520 (1929) showed that the immunogenicity of pneumococcus type 3 polysaccharide could be increased by binding it chemically to a carrier protein. This principle has been applied successfully to increase the immunogenicity of polysaccharides of other pathogens. Methods to couple covalently polysaccharides to protein carriers are known in the art and include the following:

Gu, X., et al., "Synthesis, Characterization, and Immunologic Properties of Detoxified Lipooligosaccharide from Nontypeable *Haemophilus influenza* Conjugated to Proteins", *Infection and Immunity*, 64 (10), (1996) pp. 4047-4053.

Gupta, R., et al., "Comparative Immunogenicity of Conjugates Composed of *Escherichia coli* 01110-Specific Polysaccharide, Prepared by Treatment with Acetic Acid or Hydrazine, Bound to Tetanus Toxoid by Two Synthetic Schemes", *Infection and Immunity*, 63 (8), (1995), pp. 2805-2810.

Gupta, R., et al., "Synthesis, Characterization, and Some Immunological Properties of Conjugates Composed of the Detoxified Lipopolysaccharide of *Vibrio cholerae* O1 Serotype Inaba Bound to Cholera Toxin", *Infection and Immunity*, 60 (8), (1992), pp. 3201-3208.

Konadu, E., et al., "Investigational Vaccine for *Escherichia coli* 0157: Phase 1 Study of O157 O-Specific Polysaccharide-*Pseudomonas aeruginosa* Recombinant Exprotein A Conjugates in Adults", *Journal of Infectious Diseases*, 177, (1998), pp. 383-387.

Konadu, E., et al., "Phase 1 and Phase 2 Studies of *Salmonella enterica* Serovar Paratyphi A O-Specific Polysaccharide-Tetanus Toxoid Conjugates in Adults, Teenagers, and 2- to 4-Year Old Children in Vietnam", *Infection and Immunity*, 68 (3), (2000), pp. 1529-1534.

Konadu, E., et al., "Preparation, Characterization, and Immunological Properties in Mice of *Escherichia coli* O157 O-Specific Polysaccharide-Protein Conjugate Vaccines", *Infection and Immunity*, 62 (11), (1994), pp. 5048-5054.

Robbins, J., et al., "Polysaccharide-Protein Conjugates: A New Generation of Vaccines", *The Journal of Infectious Diseases*, 161, (1990), pp. 821-832.

Taylor, D., et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (Plesiomonas shigelloides) Bound to Bacterial Toxoids", *Infection and Immunity*, 61, (1993), pp. 3678-3687.

WO119991003871; U.S. Pat. No. 4,771,127; U.S. Pat. No. 5,866,132.

In another embodiment, the invention relates to conjugates wherein *Shigella* O polysaccharide is coupled through a spacer to either IcsP or SigA to enhance antigenicity and immunogenicity of the polysaccharide and the conjugate is used to induce an immune response to both the protein and the polysaccharide.

In yet another embodiment, the *Shigella* IcsP and SigA proteins can be chemically conjugated or are the products of genetic fusion with other proteins for use as immunogens in, for example, vaccines. Such proteins include tetanus toxoid, diptheria toxoid, cholera toxin B subunit, *E. coli* enterotoxin B subunit, and flagellin. These proteins are well known in the art and have been extensively used for these purposes in the industry and/or research as set forth in the following publications:

S J McKenzie and J F Halsey Cholera toxin B subunit as a carrier protein to stimulate a mucosal immune response. The Journal of Immunology, Vol 133, Issue 41818-1824, S. Shah, R. Raghupathy, Om. Singh, G. P. Talwar and A. Sodhi. Prior immunity to a carrier enhances antibody responses to hCG in recipients of an hCG-carrier conjugate vaccine. Vaccine, Volume 17, Issues 23-24, 1999, Pages 3116-3123

LE MOIGNE Vincent; ROBREAU Georges; MAHANA Wahib; Flagellin as a good carrier and potent adjuvant for Th1 response: Study of mice immune response to the p27 (Rv2108) *Mycobacterium tuberculosis* antigen. Molecular immunology 2008, vol. 45, n°9, pp. 2499-2507

Camilo Cuadros, Francisco J. Lopez-Hernandez, Ana Lucia Dominguez, Michael McClelland, and Joseph Lustgarten. Flagellin Fusion Proteins as Adjuvants or Vaccines Induce Specific Immune Responses. Infection and Immunity, May 2004, p. 2810-2816, Vol. 72, No. 5.

In yet another embodiment, the invention relates to conjugates wherein the polysaccharide of another enteropathogenic bacteria such as *Salmonella typhi* Vi polysaccharide or *Salmonella paratyphi* is covalently coupled through a spacer to either IcsP or SigA, and the conjugate is used to induce an immune response to both the protein and the polysaccharide and thus to vaccinate against both shigellosis and typhoid (or paratyphoid) disease.

The present invention also provides methods to produce anti-Shigella IcsP2 and SigA2 antibodies in animals and recombinant polypeptides for use in diagnostic methods for detecting *Shigella* in patients known or suspected of having shigellosis. Such antibodies present in the sera of immunized mice and guinea pigs can also be produced in other animal species, such as horse, goat, rabbit, monkey, cattle, donkey, hamster. Molecular biology and antibody technology, such as that involving the use of hybridomas, has made available to researchers and clinicians sources of highly specific and potent monoclonal antibodies useful in general diagnostic and clinical procedures. Such monoclonal antibodies can be obtained by standard fusion of immune cells from an animal immunized with either IcsP2 or SigA2 with appropriate myeloma cells. More specifically, nucleic acid, protein or peptide molecules of the invention may be utilized to develop monoclonal or polyclonal antibodies that bind *Shigella* IcsP2 or SigA2. For preparation of the *Shigella* IcsP2- or SigA2-binding antibodies of the present invention, any technique which provides for the production of antibody molecules by continuous cell lines in culture may be used. For example, the hybridoma technique originally developed by Kohler and Milstein (256 Nature 495-497 (1975)) may be used. See also U.S. Pat. No. 4,376,110; Ausubel et al., Antibodies: a Laboratory Manual, (Harlow & Lane eds., Cold Spring Harbor Lab. 1988); Current Protocols in Immunology, (Colligan et at., eds., Greene Pub. Assoc. & Wiley Interscience N.Y., 1992-1996).

Another advantageous route for creating high affinity and/or high avidity human antibodies involves antigen priming of native human lymphocytes in vitro, transferal of the resultant in vitro antigen primed lymphocytes to an immunocompromised donor, e.g., a SCID mouse, boosting the immunocompromised donor with antigen, isolating human antibody secreting B-cells (IgG secreting) from the donor, and EBV-transforming the isolated human antibody secreting cells, as described in U.S. Pat. No. 6,537,809.

The antibodies of the present invention include chimeric antibodies comprising part human and part mouse antibodies, in which the constant region from human antibodies are cloned to a variable regions of light and heavy chains from mouse. In some instances, 70% of the human sequences are retained. Humanized antibodies are chimeric antibodies in which perhaps 90% of the human antibody framework is retained, and combined only with the murine the complementary determining regions. Fully humanized antibodies are also contemplated in the present invention.

Recombinant murine or chimeric murine-human or human-human antibodies that bind an epitope included in the amino acid sequences of *Shigella* IcsP2 or SigA2 can be provided using known techniques. See, e.g., Current Protocols in Molecular Biology (Ausubel et al., eds. Wiley Interscience, N.Y., 1987, 1992, 1993); Sambrook et al. Molecular Cloning: A Laboratory Manual (Cold Spring Harbor Lab. Press 1989); EP0239400.

Anti-Shigella IcsP2 and SigA2 antibodies and/or peptides of the present invention are useful for immunoassays which detect or quantitate *Shigella* IcsP2 and SigA2, or anti-Shigella IcsP2 and SigA2 antibodies, in a sample. An immunoassay for *Shigella* IcsP2 and SigA2 typically comprises incubating a clinical or biological sample in the presence of a detectably labeled high affinity (or high avidity) anti-Shigella IcsP2 or SigA2 antibody or polypeptide of the present invention capable of selectively binding to IcsP2-specific antibodies or SigA2-specific antibodies, and detecting the labeled peptide or antibody which is bound in a sample. Various clinical assay procedures are well known in the art. See, e.g., Immunoassays for the 80's (Voller et al., eds., University Park, 1981). Such samples include tissue blood, serum, and fecal samples, or liquids collected from the colorectal track following enema or oral laxative solution and subjected to ELISA analysis as described below.

Thus, an anti-Shigella IcsP2 or SigA2 antibodies or *Shigella* IcsP2 and SigA2 polypeptides can be fixed to nitrocellulose, or another solid support which is capable of immobilizing soluble proteins. The support can then be washed with suitable buffers followed by treatment with the detectably labeled *Shigella* IcsP2 and SigA2-specific peptide or antibody. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinyl fluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to *Shigella* IcsP2 and SigA2 or an anti-*Shigella* IcsP2 or anti-*Shigella* SigA2 antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation.

Well known method steps can determine binding activity of a given lot of anti-*Shigella* IcsP2 and SigA2 peptide and/or antibody. Those skilled in the art can determine operative and optimal assay conditions by routine experimentation.

Detectably labeling a *Shigella* IcsP2- or SigA2-specific peptide and/or antibody can be accomplished by linking to an enzyme for use in an enzyme immunoassay (ETA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the *Shigella* IcsP2- and SigA2-specific antibodies of the present invention include, but are not limited to, horseradish peroxidase, alkaline phosphatase, glucose oxidase, beta-galactosidase, glucose-6-phosphate dehydrogenase, glucoamylase and acetylcholinesterase.

By radioactively labeling the *Shigella* IcsP2- and SigA2-specific antibodies, it is possible to detect *Shigella* IcsP2 and SigA2 through the use of a radioimmunoassay (RIA). See Work et al., LABORATORY TECHNIQUES & BIOCHEMISTRY IN MOLECULAR BIOLOGY (North Holland Publishing Co., N.Y. (1978). The radioactive isotope can be detected by such means as the use of a gamma counter or a scintillation counter or by autoradiography. Isotopes which are particularly useful for the purpose of the present invention are: $^3H$, $^{131}I$, $^{35}S$, $^{14}C$, and $^{125}I$.

It is also possible to label the *Shigella* IcsP2- and SigA2-specific antibodies with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The *Shigella* IcsP2 and SigA2-specific antibodies can also be detectably labeled using fluorescence-emitting metals such as $^{125}Eu$, or others of the lanthanide series. These metals can be attached to the *Shigella* IcsP2- and SigA2-specific antibodies using such metal chelating groups as diethylenetriaminepentaacetic acid (DTPA) or ethylenediamine-tetraacetic acid (EDTA).

The *Shigella* IcsP2- and SigA2-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the *Shigella* IcsP2- and SigA2-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the *Shigella* IcsP2- and SigA2-specific antibodies, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the *Shigella* IcsP2 and SigA2 which is detected by the above assays can be present in a biological sample. Any sample containing *Shigella* IcsP2 or SigA2 can be used. For example, the sample is a biological fluid such as, for example, blood, serum, urine, feces, a tissue extract or homogenate, and the like. However, the invention is not limited to assays using only these samples, it being possible for one of ordinary skill in the art to determine suitable conditions which allow the use of other samples.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, immunometric assays include "forward" assays in which the antibody bound to the solid phase is first contacted with the sample being tested to extract the *Shigella* IcsP2- or SigA2-containing proteins from the sample by formation of a binary solid phase antibody-Shigella IcsP2 or SigA2 complex. After a suitable incubation period, the solid support is washed to remove the residue of the fluid sample, including unreacted *Shigella* IcsP2 or SigA2, if any, and then contacted with the solution containing a known quantity of labeled antibody (which functions as a "reporter molecule"). After a second incubation period to permit the labeled antibody to complex with the *Shigella* IcsP2 or SigA2 bound to the solid support through the unlabeled antibody, the solid support is washed a second time to remove the unreacted labeled antibody. This type of forward sandwich assay can be used to determine whether *Shigella* IcsP2 and/or SigA2 is present or can be made quantitative by comparing the measure of labeled antibody with that obtained for a standard sample containing known quantities of *Shigella* IcsP2 and SigA2. Such "two-site" or "sandwich" assays are described by Wide, Radioimmune Assay Methods, 199-206 (Kirkham, ed., Livingstone, Edinburgh, 1970).

Other type of "sandwich" assays, which can also be useful with *Shigella* IcsP2 and SigA2, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

In accordance with the present invention there may be numerous tools and techniques within the skill of the art, such as those commonly used in molecular immunology, cellular immunology, pharmacology, and microbiology. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), and "IU" means International Units.

"Polymerase chain reaction" is abbreviated PCR; "Reverse transcriptase polymerase chain reaction" is abbreviated RT-PCR; "Untranslated region" is abbreviated UTR; "Sodium dodecyl sulfate" is abbreviated SDS; and "High Pressure Liquid Chromatography" is abbreviated HPLC.

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., 3rd ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDT A at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual*, $2^{nd}$ ed., vol. 2, ch. 9.50, CSH Laboratory Press, 1989; Ausubel et al. (eds.), 1989, *Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

A "host cell" includes an individual cell or cell culture which can be or has been a recipient for vector(s) or for incorporation of polynucleotide molecules. In the present invention, a host cell can be a bacteria, a mammalian cell, an insect cell or a yeast cell.

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

An "immune response" refers to the development in the host of a cellular and/or antibody-mediated immune response to a composition or vaccine of interest. Such a response usually consists of the subject producing antibodies, B cells, helper T cells, and/or cytotoxic T cells directed specifically to an antigen or antigens included in the composition or vaccine of interest. The immune response also may include regulatory T-cells, whose activity is beyond the organism of interest, and may suppress other immune or allergic responses.

A "therapeutically effective amount" means the amount of a compound, adjuvant, or vaccine composition that, when administered to a mammal for treating a state, disorder or condition, is sufficient to effect such treatment. The "therapeutically effective amount" will vary depending on the compound, bacteria or analogue administered as well as the disease and its severity and the age, weight, physical condition and responsiveness of the mammal to be treated.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine.

In a preferred embodiment, the pharmaceutical composition is conveniently administered as a liquid oral formulation. Although there are no physical limitations to delivery of the formulation, oral delivery is preferred because of its ease and convenience, and because oral formulations readily accommodate additional mixtures, such as milk, yogurt, and infant formula. Other oral dosage forms are well known in the art and include tablets, caplets, gel caps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are generally regarded as physiologically tolerable.

"Patient" or "subject" refers to mammals and includes human and veterinary subjects.

The dosage of an adjuvant formulation or vaccine composition containing the adjuvant will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as monthly or annually to maintain an effective immunological memory.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The invention also encompasses pharmaceutical compositions and vaccines. The pharmaceutical compositions and vaccine compositions of the invention comprise at least one of the novel *Shigella* antigens, and one or more adjuvants along with a pharmaceutically acceptable carrier or excipient. Methods of formulating pharmaceutical compositions and vaccines are well-known to those of ordinary skill in the art, as described in Remington's, supra.

Formulations. The compositions of the present invention may comprise pharmaceutically acceptable diluents, preservatives, solubilizers, emulsifiers, adjuvants and/or carriers. Such compositions include diluents of various buffer content (e.g., Tris-Hel, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435-1712 which are herein incorporated by reference.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid micro spheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PV AP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, β-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrates include but are not limited to starch, including the commercial disintegrant based on starch, Explotab, Sodium starch glycolate, Amberlite, sodium carboxymethyl cellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrantsBinders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention. The therapeutic agent could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the therapeutic agent is enclosed in a semipermeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

In one embodiment, the *Shigella* polypeptide antigens disclosed in the present invention are administered with a pharmaceutically acceptable diluent. Such formulations can be administered by an injection (subcutaneous, intradermal, intramuscular) or applied topically onto the skin using an adhesive patch. Alternatively, the vaccine is administered by a mucosal route (oral, buccal, sublingual, nasal drops, aerosol, rectal) using a pharmaceutically acceptable vehicle. The antigens can also be mixed with an adjuvant to enhance the ensuing immune responses. Example of such adjuvants are without being limited to, aluminium salts, ISCOMs, saponin-based adjuvants, oil-in-water and water-in-oil emulsions, toll-like receptor ligands such as muramyl dipeptide, *E. coli* LPS, oligonucleotides comprised of unmethylated DNA, poly I:C, lipoteichoic acid, peptidoglycan. Enterotoxins and their adjuvant active derivatives such as cholera toxin, heat-labile *E. coli* enterotoxin, pertussis toxin, shiga toxin and analogs Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Vaccines. In the case of vaccines, it is often observed that a primary challenge with an antigen alone, in the absence of an adjuvant, will fail to elicit a humoral or cellular immune response. Therefore the vaccines of the invention may contain adjuvants including, but not limited to, cholera toxin, fragments and mutants or derivatives with adjuvant properties, *Escherichia coli* heat-labile enterotoxin, fragments and mutants or derivatives with adjuvant properties, oil-in-water and water-in-oil emulsions, toll-like receptor ligands such as muramyl dipeptide, *E. coli* LPS, oligonucleotides comprised of unmethylated DNA, poly I:C, lipoteichoic acid, peptidoglycan. Enterotoxins and their adjuvant active derivatives such as cholera toxin, heat-labile *E. coli* enterotoxin, pertussis toxin, shiga toxin and analogs. Other adjuvants can be used such as complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (*bacille Calmette-Guerin*) and *Corynebacterium parvum*. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Where the vaccine is intended for use in human subjects, the adjuvant should be pharmaceutically acceptable.

Administration. Such pharmaceutical compositions or vaccines may be for administration by oral (solid or liquid), parenteral (intramuscular, intraperitoneal, intravenous (IV) or subcutaneous injection), transdermal (either passively or using ionophoresis or electroporation), transmucosal (nasal, vaginal, rectal, or sublingual), or inhalation routes of administration, or using bioerodible inserts and can be formulated in dosage forms appropriate for each route of administration.

In one preferred embodiment, the compositions or vaccines are administered by pulmonary delivery. The composition or vaccine is delivered to the lungs of a mammal while inhaling and traverses across the lung epithelial lining to the blood stream [see, e.g., Adjei, et al. Pharmaceutical Research 1990; 7:565-569; Adjei, et al. Int. J. Pharmaceutics 1990; 63:135-144 (leuprolide acetate); Braquet, et al. J. Cardiovascular Pharmacology 1989; 13 (sup5):143-146 (endothelin-1); Hubbard, et al. (1989) Annals of Internal Medicine, Vol. III, pp. 206-212 ($\alpha$1-antitrypsin); Smith, et al. J. Clin. Invest. 1989; 84: 1145-1146 ($\alpha$-1-proteinase); Oswein, et al. "Aerosolization of Proteins", 1990; Proceedings of Symposium on Respiratory Drug Delivery II Keystone, Colo. (recombinant human growth hormone); Debs, et al. J. Immunol. 1988; 140:3482-3488 (interferon-$\gamma$ and tumor necrosis factor $\alpha$); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al. See also U.S. Pat. No. 6,651,655 to Licalsi et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, NC); and the Spinhaler powder inhaler (Fisons Corp., Bedford, Mass.). All such devices require the use of formulations suitable for the dispensing of the therapeutic agent. Typically, each formulation is specific to the type of device employed and may involve the use of an appropriate propellant material, in addition to the usual diluents, adjuvants, surfactants and/or carriers useful in therapy. Also, the use of liposomes, microcapsules or microspheres, inclusion complexes, or other types of carriers is contemplated.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydro chlorofluorocarbon, a hydro fluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in particulate form with an average particle size of less than 10 mm (or microns), most preferably 0.5 to 5 mm, for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition or vaccine of the present invention may be administered in conjunction with one or more additional active ingredients, pharmaceutical compositions, or vaccines. The therapeutic agents of the present invention may be administered to an animal, preferably a mammal, most preferably a human.

Dosages

Following methodologies which are well-established in the art, effective doses and toxicity of the compounds and compositions of the instant invention, which performed well in in vitro tests, are then determined in preclinical studies using small animal models (e.g., mice or rats) in which the Shigella antigens, polypeptide, pharmaceutical, or vaccine compositions have been found to be therapeutically effective and in which these drugs can be administered by the same route proposed for the human clinical trials.

Formulations or dosage forms for use in the present invention need not contain a therapeutically effective amount of the components disclosed here because such therapeutically effective amounts can be achieved by administering a plurality of such formulations or dosage forms.

For any pharmaceutical composition used in the methods of the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical trial.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, and seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

The data obtained from animal studies can be used in formulating a range of doses for use in humans. The therapeutically effective doses of in humans lay preferably within a range of circulating concentrations that include the $ED_{50}$ with little or no toxicity. The dosage can vary within this range depending upon the dosage form employed and the route of administration utilized. Ideally, a single dose of each drug should be used daily.

The following describes materials and methods employed in Examples 1-14.

Materials and Methods

Cloning, Expression and Purification of Shigella SigA2 and Icsp2 Polypeptides

DNA sequences of the protein antigens are available as described above (37). SigA DNA sequence of S. flexneri 2a strain 2457T was obtained from the gene bank accession number [Genbank AE014073]. The DNA sequence of icsP of S. flexneri 5a strain M90T was also obtained from the gene bank accession number [Genbank AL391753]. The nucleotide identity and amino acid sequence homology among different species of Shigella are more than 99%. The DNA fragments were inserted into a commercially available E. coli over-expression plasmid pET21d (Novagen, Gibbstown, N.J., USA) and purified according to the manufacturer's instruction using TALON metal-affinity resin (Clontech, Mountain View, Calif., USA).

Primers:

IcsP2 primer set CCGGAATTCGG AGTGAAAACGGGGGGAGC and CGGCGGCTC-GAGCTAGTGGTGGTGGTGGTGGTG AATACTTGCACTATTTTT was used for amplification if IcsP2 fragment from S. flexneri 2a 2457T strain. The amplified fragment (SEQ ID NO:1, 390 bp, underlined sequence) was digested with EcoRI and XhoI (boxed sequence, as shown in FIG. 12).

```
SigA2 primer set
CCCGGGGAATTCGGGAAAAAGCCTTCAATAAAA
and

CGGCGGCTCGAGCTAGTGGTGGTGGTGGTGGTGGTTGAAACTACTTTCGC

CTG
``` was used for amplification of SigA2 fragment from S. flexneri 2a 2457T strain. The amplified fragment (SEQ ID NO:3, 795 bp, underlined sequence) was digested with EcoRI and XhoI (boxed sequence, as shown in FIG. 13).

Amplified IcsP2 fragment and SigA2 fragments were inserted into EcoRI and XhoI site of pET21d and the recombinant DNA was verified with sequencing. The E. coli BL21 (DE3) (Novagen, Gibbstown, N.J., USA) bacteria were transformed with each recombinant plasmid and the protein over-expression was induced by 0.5 mM IPTG (Isopropyl-β-D-Thiogalactopyranoside) in the media at 37° C. E. coli BL21 (DE3) overexpressing each fragment was harvested and disrupted by freeze/thaw followed by sonication in the presence of 6 M urea. The E. coli extract was centrifuged by 12,000×g and the supernatant was loaded on the pre-equilibrated (with 1× binding buffer: 20 mM TrisCl pH 7.9, 500 mM NaCl 5 mM immidazole and 6 M urea) TALON resin column (3 ml). The column was washed with 20 ml of 1× binding buffer and 30 ml of 1× washing buffer (20 mM TrisCl pH 7.9, 500 mM NaCl, 15 mM immidazole and 6 M urea) and the protein was eluted by 1× elution buffer (20 mM TrisCl pH 7.9, 500 mM NaCl, 250 mM immidazole).

One other fragment of IcsP was also subcloned as described above (Primer set CCCGGGGAATTCACCAC-TAACTATCCACTTTT and CGGCGGCTCGAGCTAGTG-GTGGTGGTGGTG ACTGTAACGACTCTCTTGGTA)

icsP and sigA gene disrupted mutant strains (S. flexneri 2a 2457T background) construction: icsP and sigA gene disrupted mutant strains were constructed individually by using an allele exchange method (17). Briefly, the internal 300 nt DNA fragments of icsP and sigA (from nucleotide 61 to 360) were amplified with primers Ics5Tr/lcs3Tr (5'-GGC TCT AGA ACCACTAACTATCCACTT-3'/5'-GCC GAA TTC CCA GCT CTG GTC GGT CCA-3') for icsA fragment and Sig5Tr/Sig3Tr (5'-GGC TCT AGA GAA CTG ACC CGG AAA GTT AGT-3'/5'-GCC GAA TTC GTA CGC ACC TCC TAA TGA—3') for sigA fragment. These fragments were inserted into a suicide plasmid pSW23.oriT. The recombinant plasmid pSWicsPTr and pSEsigATr were used to transform E.

coli strain BW19610 (pir+ Amp$^s$ Cm$^r$). Each plasmid was purified from BW19610, and used to transform *E. coli* SM10λpir (pir+ Tra+ Amp$^s$ Cm$^r$). *E. coli* SM10λpir was conjugated with *S. flexneri* 2a 2457T and the chloramphenicol resistant *S. flexneri* was isolated on a Congo Red/streptomycin/chloramphenicol plate. In each knockout strain, the gene on the virulence plasmid and the genome are split into two fragments: 5' end fragment of 360 nucleotides and 3' end fragment. This disruption of each gene on the mutant strains was confirmed by PCR and sequencing. Each strain was used for challenging the immunized mice.

Three other fragments of SigA protein were also purified as describe above using primer sets as: SigA1 fragment primer set: CCCGGGGAATTCGGTATGGCGAAACAGCATTTGC and CGGCGGCTCGAGCTAGTGGTGGTGGTGGTGGTG CTCTTGTTTTTTACCATCCA (824 bp fragment using EcoRI and XhoI), SigA3 fragment primer set CCGGGGAAGCTTGACCCCTACAGAAAATAATA and CGGCGGCTCGAGCTAGTGGTGGTGGTGGTGGTG CTCGCCATTGGTGTCACGCA (822 bp fragment using HindIII and XhoI), and SigA4 fragment primer set CCCGGGGAATTCGGGATAAAAAACATGAGCTGG and CGGCGGCTCGAGCTAGTGGTGGTGGTG-GTGGTGGAAAGAGTAACGGAAGTTGG (702 bp fragment using EcoRI and XhoI). These fragments were overexpressed and purified as described above. The SigA1 fragment showed immunogenicity but no protection while SigA3 and SigA4 fragments did not provoke antibody responses in mice. All the primers were purchased from Genotech, Taejon, Korea.

Bacterial Strains

*S. flexneri* 2a strain 2457T and *S. flexneri* 5a strain M90T were provided by Dr. Philippe Sansonetti, Institut Pasteur, Paris, France).

*S. boydii* (IB8295) serotype 1: was obtained from a Shigellosis patient in Pakistan collected in 2002 (IVI collection).

*S. sonnei* (IB4200): was obtained from a Shigellosis patient in India collected in 2004 provided by Dr. G. B. Nair (NICED, India).

*S. dysenteriae* serotype 1: was provide by Dr. D. Kopecko (FDA, Bethesda, Md., USA).

Animal Immunizations

All animals were maintained under specific pathogen-free conditions in the animal care facilities of the International Vaccine Institute (Seoul) in accordance with International guidelines and all experiments described here were approved by the International Vaccine Institute ethical committees for animal experimentation.

For the purpose of this invention, an immunologic adjuvant is defined as "any substance that acts to accelerate, prolong, or enhance antigen-specific immune responses when used in combination with specific vaccine antigens" (The Use of Conventional Immunologic Adjuvants in DNA Vaccine Preparations, by Shin Sasaki and Kenji Okuda. In D. B. Lowrie and R. G. Whalen (editors), DNA Vaccines: Methods and Protocols, Humana Press, 2000. ISBN 978-0-89603-580-5), as well as "a substance used to help boost the immune response to a vaccine so that less vaccine is needed (Definition of Adjuvant, National Cancer Institute). Cholera toxin, oligodeoxynucleotides which contain unmethylated CpG motifs (CpG ODN), and aluminium salts are known adjuvants, when co-administered with antigens.

Five to six week old female Balb/c mice were immunized with the protein antigens administered by various routes. Dose: for each immunization, a dose of 25 μg of the protein antigens was mixed with an adjuvant in isotonic, pyrogen-free, phosphate-buffered saline, pH 7.4 (PBS). The adjuvant consisted of either cholera toxin (CT) (3 to 5 micrograms μg) per dose), CpG ODN (4 μg per dose), or aluminium hydroxide (alum).

Intra-Peritoneal Administration

25 μg of protein antigen was administered by intraperitoneal injection, with or without adjuvant, in a total volume of 0.2 ml of PBS. Mice were immunized three times, at two weeks intervals.

Intranasal Administration

25 μg of protein antigen was mixed with 3 μg of cholera toxin (CT) and administered through each nostril in a total volume of 50 microliters (approximately 25 microliter per nostril). Two and four weeks later, mice were re-immunized under identical conditions.

Rectal Administration

100 μg protein antigen was mixed with CT (5 microgram) and administered in a final volume of 0.2 milliliters with a pipette inserted into the anorectal orifice. Guinea pigs were immunized three times, at two weeks interval between each immunization.

Animal Models of Shigellosis

Mouse pneumonia model: $2 \times 10^7$ CFU of *S. flexneri* 2a strain 2457T in 50 microliters of PBS were inoculated into the nostrils of immunized mice. Animals were monitored daily for 10 days. *S. flexneri* 5a strain M90T and *S. dysenteriae* 1 strains were also used for challenge experiment.

Guinea pig keratoconjunctivitis model: One week after the last of three consecutive immunizations with *Shigella* protein antigens adjuvanted with CT, guinea pigs were anesthetized and $1 \times 10^5$ cfu/20 ul of *S. flexneri* 2a strain 2457T was instillated in the eye conjunctival sac of guinea pigs. Periocular symptoms were monitored daily for 4-5 days. For comparison with systemic immunization, 50 μg of protein was administered through Intraperitoneal route with 3 μg of CT three times two weeks interval, and the immunized Guinea pig was challenged one week after the final immunization as described.

Guinea pig colitis model: A recently developed model of intestinal shigellosis (30) was used to evaluate the protective efficacy of the novel *Shigella* common protein antigens disclosed in the present invention. Briefly, *S. flexneri* 2a 2457T ($1 \times 10^9$ CFU) or *S. flexneri* 5a strain M90T were administered by instillation through the ano-rectal orifice of 5 week old guinea pigs, as described by Shim, Suzuki, Chang et al (30). Animals were examined daily for symptoms of dysentery (diarrhea, tenesmus) and then sacrificed by pentobarbital overdose prior to histological analyses of colon tissue specimens.

Measurements of Systemic and Mucosal Immune Responses to *Shigella* Common Protein Antigens Collection of Biological Fluids Serum and secretions (saliva, vaginal and rectal washes) were collected 1 week before the first immunization and thereafter one week after each immunization.

Preparation of Organ Extracts and Isolation of Cell Suspensions

One week after the last immunization, mice were anesthetized with pentobarbital and 125 i.u. of heparin (SIGMA, MO, USA) in 0.2 ml saline was injected intra-peritoneally. Blood was drawn directly from the heart and the mice were sacrificed by cervical dislocation. Mice were perfused by injecting 15 ml of PBS containing heparin (10 i.u./ml) into the heart right ventricle until the lungs were inflated and turned clear. Finely cut lung fragments were digested for 30 min at 37° C. with collagenase A (0.5 mg/ml) (Roche) in RPMI medium (Gibco Europe, U.K.) supplemented with DNase 1 (0.1 mg/ml) (Roche) and single cell suspensions were collected by filtration through a cell strainer. Single cell suspensions from spleen were obtained by pressing the organs through nylon sieves. All suspensions were freed from erythrocytes by treatment with ammonium chloride, washed, resuspended in RPMI medium containing 5% FBS, and stored on ice until being assayed (within 30 minutes) by means of the ELISPOT assay described below.

For preparation of cell-free organ extracts, the PERFEXT technique (34) was used. Lungs from perfused animals were excised and sliced into small (2-3 mm thick) fragments and further perfused by incubation for 30 minutes at 37° C. in PBS containing heparin, under constant agitation. Fragments were pelleted by centrifugation (500 rpm, 3 minutes) and resuspended in extraction buffer, consisting of Triton X100, PMSF and protease inhibitors (34). Samples were snap frozen in liquid nitrogen and stored at −70° C. Prior to use, samples were thawed at room temperature and centrifuged (2000 rpm, 5 minutes). Supernatants were collected and assayed for specific antibody activity by means of ELISA, as described below.

Antibody ELISA (Enzyme Linked Immunosorbent Assay)

The levels of antibodies to *Shigella* common protein antigens in sera, in secretions and in tissue PERFEXT extracts, were estimated by standard solid phase enzyme-linked immunosorbent assay (ELISA). Individual wells of polystyrene 96-well plates (NUNC, Denmark) were coated with each protein (1 microgram per ml of PBS; 0.1 ml per well; overnight incubation at ambient temperature), blocked with 5% (vol/vol) skim milk in PBS containing 0.05% Tween 20 (0.2 ml per well; 30 minutes at ambient temperature) and washed three times with PBS-Tween. Serial two-fold dilutions of samples in PBS-Tween with 5% skim milk solution were incubated in antigen-coated wells for 2 hrs at ambient temperature, and the plates were washed three times with PBS-Tween to remove unbound antibodies. Next, 0.1 ml of PBS-Tween containing appropriately diluted (1/5000) horseradish peroxidase-conjugated goat anti-mouse IgA or IgG antibodies (Southern Biotechnology, Birmingham, Ala., USA) was added to individual wells. The plates were then washed three times with PBS and enzyme-bound activity was monitored after addition of a chromogenic enzyme substrate. Color development was stopped by adding 50 µl of 0.5 N $H_2SO_4$, and measured spectrophotometrically ($O.D_{450}$) using an ELISA reader. Data are expressed as geometric mean antibody titers, a titer being defined as the reciprocal of the highest dilution of a sample yielding an absorbance value equal or above that of control (no sample) added.

ELISPOT assay: The frequency of cells producing specific antibodies to *Shigella* protein antigens was determined by means of the enzyme-linked immunospot (ELISPOT) assay (4). For comparison, the frequency of cells producing antibodies to cholera toxin (CT) was determined when applicable. Briefly, 10 µg of cholera toxin, 50 µg of sigA2, and 100 µg of sigA2 protein diluted in PBS were added to individual wells of nitrocellulose-bottomed 96 wells HA plates (Millipore, Bedford, USA). After overnight incubation at 4° C., each well was washed with PBS and blocked with RPMI culture medium (GIBCO, UK) containing 10% fetal bovine serum (FBS). Lung and spleen cell suspensions from immunized mice were incubated in serial two-fold dilutions (starting at eight hundred thousand mononuclear cells per well) in RPMI medium with FBS. After a 4 hrs incubation at 37° C., individual wells were washed 5 times with PBS, 5 times with PBS containing 0.05% Tween 20 and then exposed for 1 hour at room temperature to 0.1 ml of PBS-Tween containing horseradish peroxidase conjugated goat antibodies to mouse IgG or mouse IgA (1:1000 dilution). After 3 washes with PBS-Tween and 4 washes with PBS, wells were exposed to chromogen substrate for 10-20 minutes until spots appeared. Plates were then washes with running tap water and dried. Spots were then enumerated using a stereomicroscope. Data were expressed as numbers of spot-forming cells (SFC) adjusted to one million cells.

Example 1

Mucosal Immunization with IcsP2 Protects Mice Against Pneumonia Induced by *Shigella flexneri* 2a Mice were immunized with IcsP2 given together with CT by the intranasal route, as described above. Animals were challenged with a lethal dose *S. flexneri* 2a strain 2457T. The results of FIG. 1 show that immunization with IcsP protein protects animals against lung challenge with *S. flexneri* 2a. From the results shown in FIG. 1, intranasal administration of a live-attenuated *S. flexneri* vaccine strain (SC602) also protected mice against challenge.

Example 2

Mucosal Immunization with IcsP2 Protects Mice Against Pneumonia Induced by Distinct Serotypes of *Shigella flexneri*

Figure 2:
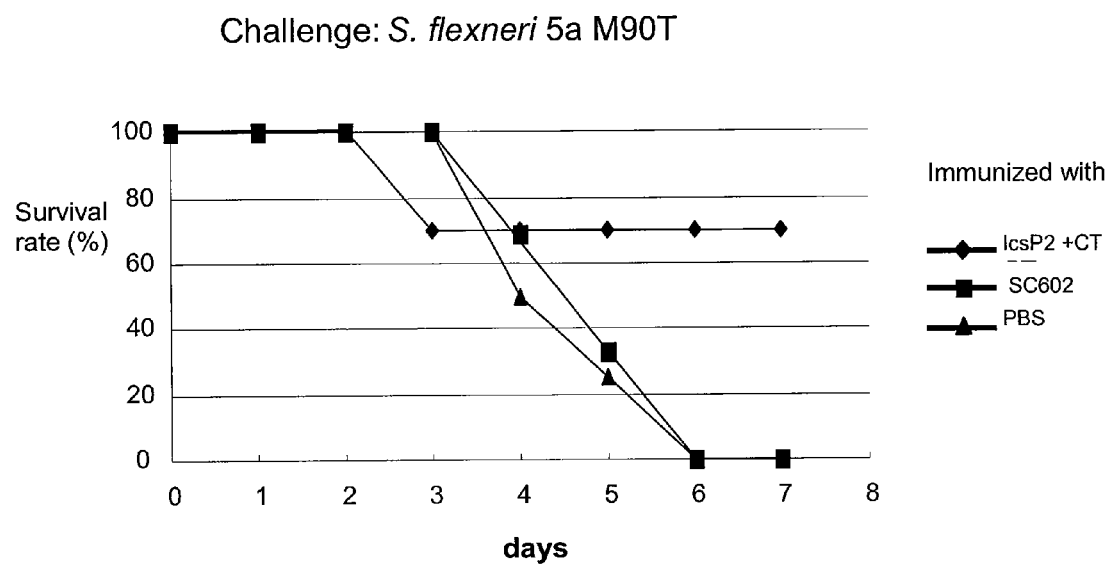
FIG. 2 shows mucosal immunization with IcsP2 and CT (IcsP2+CT) protected mice against pneumonia induced by distinct serotypes of *Shigella flexneri*

Mice were immunized with IcsP2 given together with CT by the intranasal route as described above. Animals were challenged with a lethal dose of *S. flexneri* 5a strain M90T ($2 \times 10^7$ CFU in 50 µl). The results shown in FIG. 2 indicate that immunization with IcsP protein protects animals against lung challenge with *S. flexneri* 5a. In contrast, intranasal administration of live-attenuated *S. flexneri* 2a strain (SC602) failed to protect mice against a strain of *Shigella* belonging to a different (5a) serotype (as shown by the results summarized with the filled squares in FIG. 2).

Example 3

Mucosal Immunization with IcsP2 Protects Mice Against Pneumonia Induced by *Shigella dysenteriae*

Mice were immunized with IcsP2 given together with CT by the intranasal route as described above. Animals were challenged with a lethal dose *S. dysenteriae* type 1 (strain provided by Dr. D. Kopecko, FDA, Bethesda, Md., USA).

Figure 3:
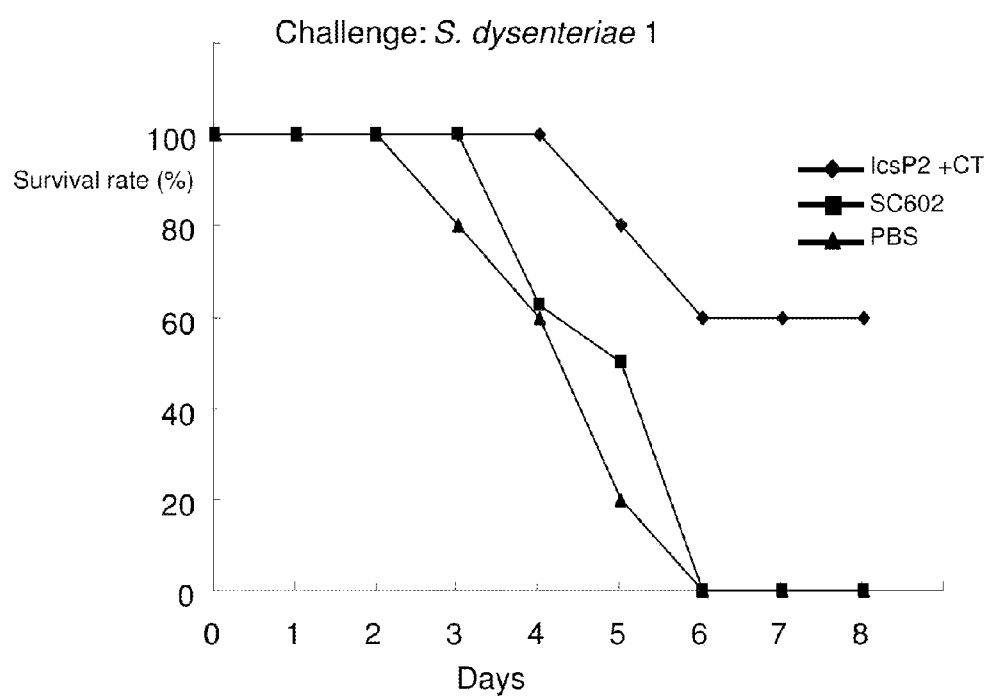
FIG. 3 shows that mucosal immunization with IcsP2 and CT (IcsP2+CT) protected mice against pneumonia induced by *Shigella dysenteriae* type 1.

The results presented in FIG. 3 demonstrate that when animals had been immunized with IcsP2, they were protected against challenge by another *Shigella* species, namely *Shigella dysenteriae* type 1. In contrast, SC602, a live-attenuated strain of *S. flexneri* 2a, failed to protect mice against lethal lung challenge with *S. dysenteriae* type 1.

From the above experiments, it can be concluded that IcsP2 not only protects against mucosal infection with *S. flexneri* belonging to distinct serotypes but also against an infection caused by a different species of *Shigella*, such as *S. dysenteriae*.

Example 4

Mucosal Immunization with SigA2 Protects Against
*S. flexneri* 2a (2457T) Challenge but not Against *S.
flexneri* Sa (M90T)

SigA protein is known to be present exclusively in *S. flexneri* 2a and not other serotypes of *S. flexneri* (1). Mice immunized with SigA2 protein were challenged with lethal dose of

Figure 4:
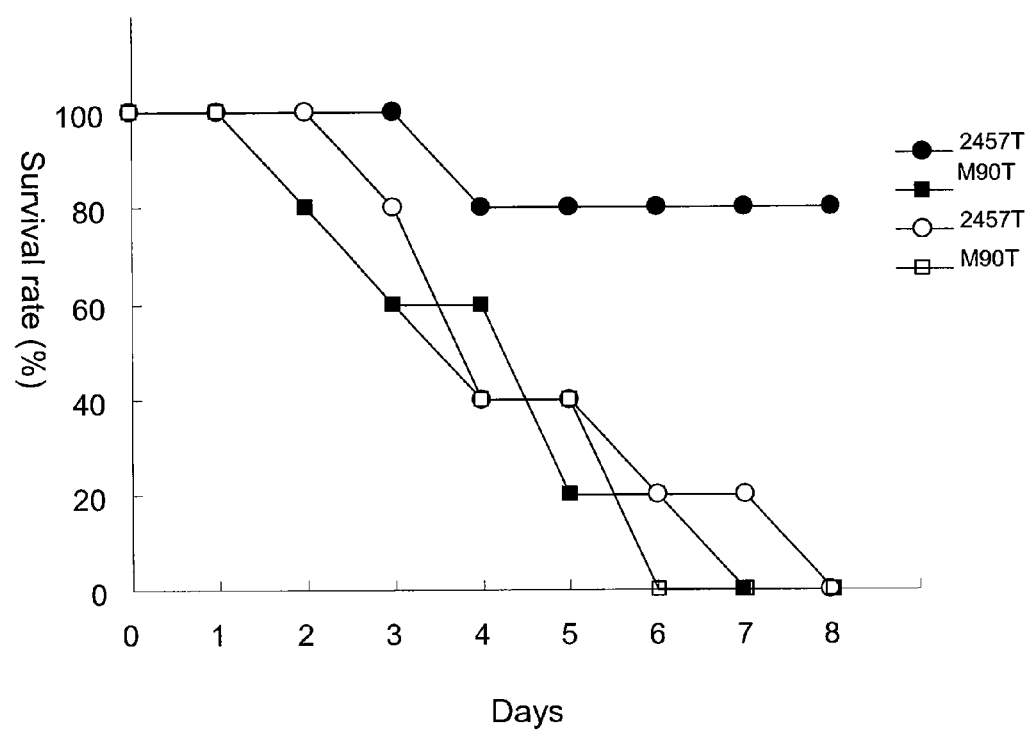
FIG. 4 shows that mucosal immunization with SigA2 protected against *S. flexneri* 2a (filled circle, 2457T) challenge but not against *S. flexneri* 5a (filled square, M90T). Mice have also been immunized with PBS in two strains 2457T (open circle) and M90T (open square) as negative controls.

*S. flexneri* 2a (2457T, filled circle) and *S. flexneri* 5a (M90T, filled square). Mice challenged with 2457T showed 80% survival while the mice challenged with *S. flexneri* died by bacteria-induced pneumonia. Mice that were immunized with PBS showed 100% death by two strains 2457T (open circle in FIG. 4) and M90T (open square in FIG. 4).

Example 5

Immunization with IcsP2 Protects Against Experimental Keratoconjunctivitis

Guinea pigs immunized with IcsP2 and control (sham immunized with PBS) as described above. Animals were challenged one week after the last of 3 consecutive immunizations with IcsP2 and CT adjuvant administered by the intranasal or the intraperitoneal route with $1 \times 10^5$ colony-forming units of virulent *S. flexneri* 2a 2457T. Guinea pigs were then examined at 24 hrs and 48 hrs after challenge for signs and intensity of ocular inflammation (keratoconjunctivitis). Animals with no detectable inflammation were considered protected. As can be seen in the Table 1 below, 40 to 50% of animals immunized with IcsP2 administered by the intranasal or by the intraperitoneal route were protected against *Shigella*-induced keratoconjunctivitis, whereas control animals (treated with PBS) all displayed keratoconjunctivitis.

TABLE 1

| antigen | Intra-peritoneal immunization | Intra-nasal immunization |
| --- | --- | --- |
| IcsP2 | 2/4 (50%)* | 2/5 (40%) |
| PBS | 4/4 (0%) | 4/4 (0%) |

*Protective efficacy: percentage of animals protected

Example 6

Immunization with IcsP2 SigA2 Protects Against *Shigella*-Induced Experimental Recto-Colitis Guinea pigs immunized with IcsP2, SigA2, SC602 and PBS were challenged with virulent *S. flexneri* 2a strain 2457T with inoculum of $1 \times 10^9$ CFU and 24 hr after the inoculation were examined for diarrhea, hemorrhage of the colon, and frequency of tenesmus. As can be seen in Table 2, all control (PBS-treated) animals had hemorrhage of the recto-colonic mucosa, most of whom had diarrhea (lack of solid feces) and presented with signs of straining at stool, also called rectal tenesmus. In contrast, animals immunized with AigA2 had no signs of recto colitis but displayed tenesmus. Animals that had been immunized with live attenuated *S. flexneri* 2a strain SC602 were protected against challenge with virulent *S. flexneri* 2a (strain 2457T). Most importantly, guinea pigs that had been immunized with purified IcsP2 were also fully protected against challenge with *S. flexneri* 2a (strain 2457T).

TABLE 2

| Group | Animal no. | Hemorrhagic rectocolitis | diarrhea | Mean frequency of tenesmus (per hour) |
| --- | --- | --- | --- | --- |
| IcsP2 | 0 | − | − | 2 |
|  | 1 | − | − |  |
|  | 2 | − | − |  |
|  | 3 | − | − |  |
| SigA2 | 0 | − | − | 12 |
|  | 1 | − | − |  |
|  | 2 | − | − |  |
| SC602 | 0 | − | − | 2 |
|  | 1 | − | − |  |
|  | 2 | − | − |  |
|  | 3 | − | − |  |
| PBS | 0 | + | + | 15 |
|  | 1 | + | − |  |
|  | 2 | + | + |  |
|  | 3 | + | + |  |

Example 7

IcsP2 Induces Protective Immunity in *Shigella*-Induced Guinea Pig Colitis Model with Different Serotypes of *S. flexneri* and *S. dysenteriae* Type 1

TABLE 3

| Challenge Strain | Protection against colitis |
| --- | --- |
| *S. flexneri* 2a | 100% |
| *S. flexneri* 5a | 100% |
| *S. dysenteriae* 1 | 80% |
| SC602 (intrarectal) | 100% |

Example 8

Figure 5:
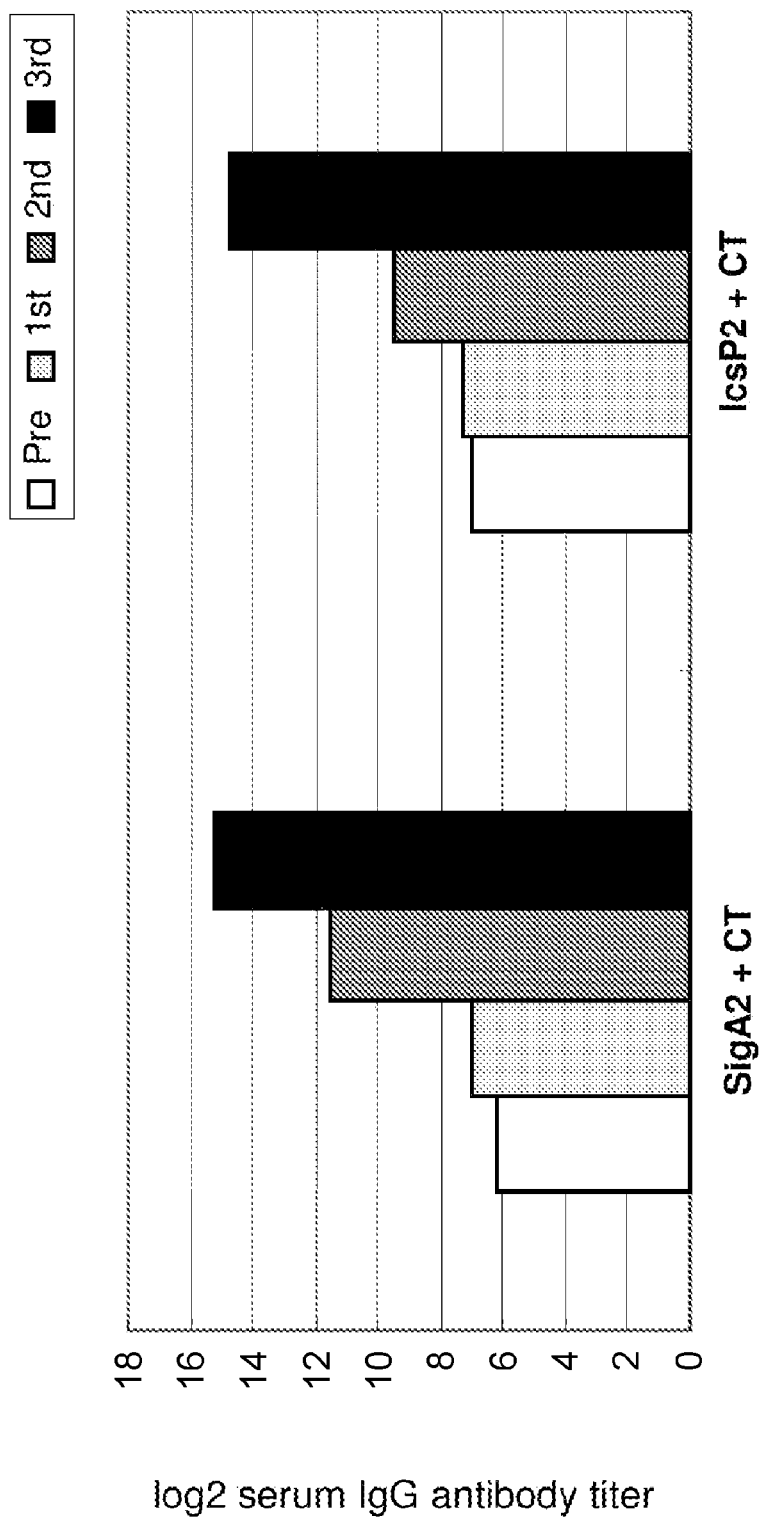
FIG. 5 shows that mucosal administration of SigA2 or IcsP2 given together with CT adjuvant induced serum antibody responses.

Mucosal Administration of SigA2 or IcsP2 Given Together with CT Adjuvant Induces Serum Antibody Responses Serum antibody levels were then determined one week after the third intranasal immunization. As can be seen in FIG. 5, mice immunized with either *Shigella* protein in the amount of 10 μg of each protein, for each immunization, mounted vigorous serum IgG antibody responses to the corresponding antigen, which were manifest already after the second immunization, being further enlarged by a third vaccination. FIG. 5 shows the antibody titers after each of 3 consecutive immunizations are shown for SigA2 and IcsP2 proteins.

Example 9

Figure 6A:
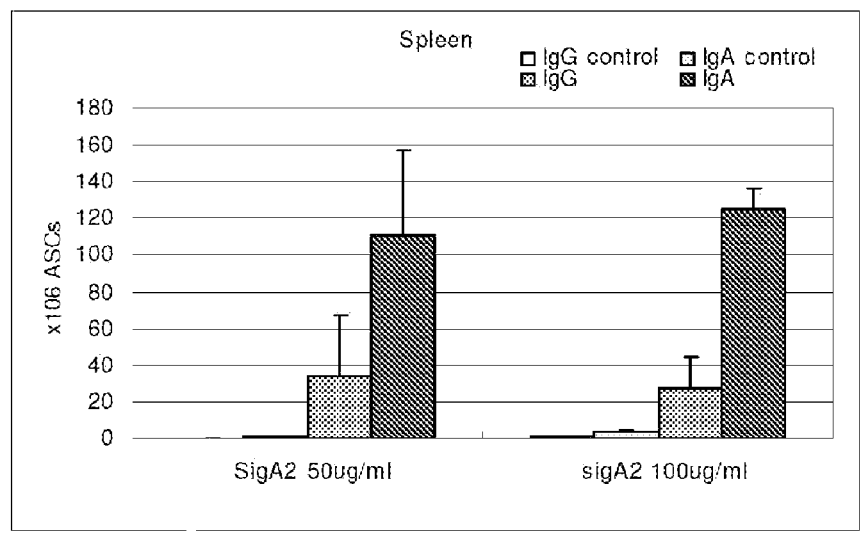
FIGS. 6A-B are graphs illustrating that animals immunized with SigA2 mounted predominantly IgA- and also IgG-ASC responses in both spleen (FIG. 6A) and lungs (FIG. 6B).
Figure 6B:
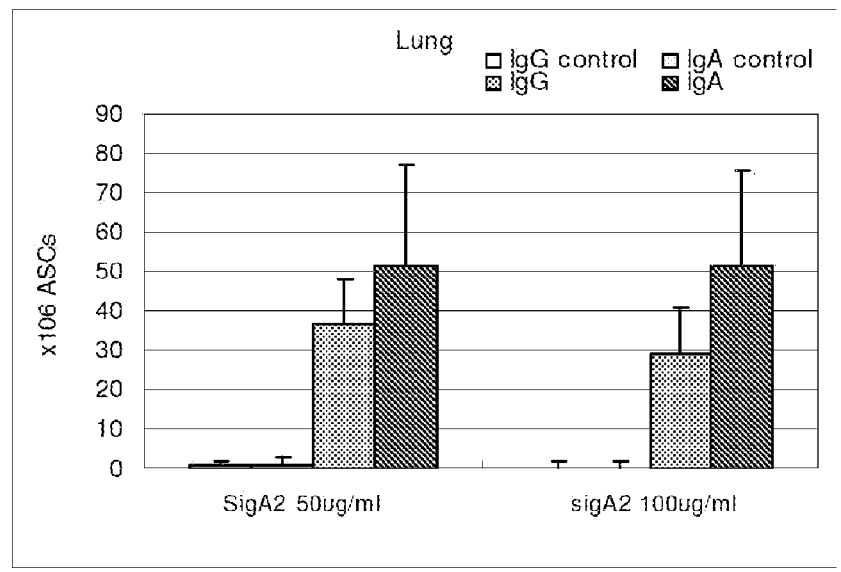

Mucosal Administration of *Shigella* Common Protein Antigens Induces Systemic and Mucosal Immune Responses Antibody-secreting cells in spleen and lung of mice immunized with SigA2 or IcsP2 were enumerated by ELIS pot assay performed on cell suspensions collected one week after 3 intra-nasal immunizations with SigA2 or IcsP2 adjuvanted with CT. Results presented in FIGS. 6A-B are expressed as mean numbers of ASCs per million mononuclear cells determined on groups of 3-4 mice (histograms) plus standard error of the mean (vertical lines). As can be seen, animals immunized with SigA2 mounted predominantly IgA- and also IgG-ASC responses in both spleen (FIG. 6A) and lungs (FIG. 6B).

Very similar findings were obtained for IcsP2-specific IgA- and IgG-ASC responses in mice immunized with IcsP2.

Figure 7:
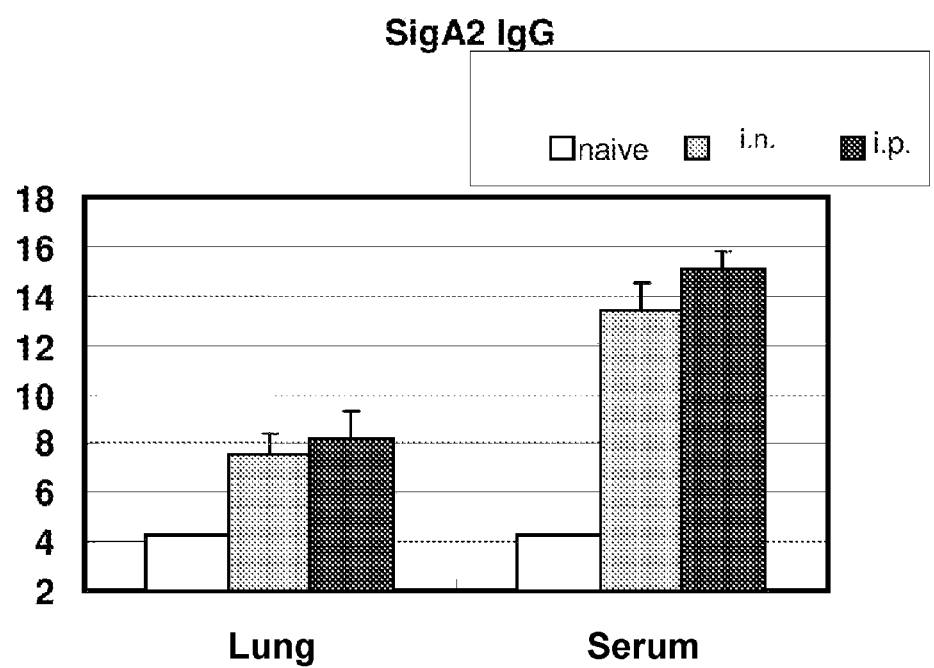
FIG. 7 is a graph illustrating that systemic (i.p.) as well as mucosal (i.n.) immunization with SigA2 induced antibody responses in the lungs and in serum.
Figure 8:
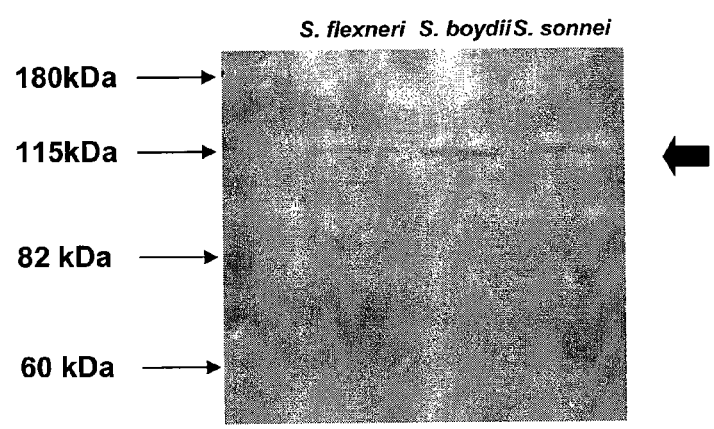
FIG. 8 shows the recognition of SigA2 protein in *Shigella* strains by mice antisera raised against SigA2 protein.

Lung extracts from mice immunized with SigA2 by the intra-nasal (i.n.) route or the intra-peritoneal (i.p.) route were assayed for SigA2-specific IgG antibody activity one week after the last of 3 consecutive immunizations. As can be seen in FIG. 7, systemic (i.p.) as well as mucosal (i.n.) immunization with SigA2 induced antibody responses in the lungs and in serum. Similar lung responses were recorded in mice immunized with IcsP2 after intranasal administration of IcsP2.

Taken together, these results demonstrate that mucosally administered SigA2 and IcsP2 are immunogenic and can induce systemic and mucosal antibody responses.

Example 10

Serum Antibodies to IcsP2 and SigA2 React with Full-Length IcsP and SigA Shigella Proteins Western blot analyses of Shigella proteins: SDS-PAGE was performed on whole cell detergent extracts of S. flexneri serotype 2a 2457T, S. boydii, S. sonnei and the proteins were transferred on nitrocellulose membranes. Membranes were incubated with mouse antisera diluted to 1/50 or 1/100 (in PBS-Tween 20 for 2 hrs at ambient temperature. These antisera were obtained by intraperitoneal injections of SigA2 and IcsP2 co-administered with alum adjuvant, as described above. After washing with PBS-Tween, the membranes were further incubated with alkaline phosphatase-conjugated goat antibodies to mouse Ig (Southern Biotech, Birmingham, Ala., USA). After washing, membranes were developed by adding BCIP-NBT chromogen substrate. For comparative purposes, separate membranes were stained with Coomassie Blue. As can be seen in FIGS. 9A and 9B, antiserum raised against SigA2 and IcsP2 can recognize full length SigA and IcsP2 (arrow corresponding to the position of the proteins) of different Shigella species (S. flexneri 2a, S. boydii, S. sonnei, and S. dysenteriae).

Example 11

In Vitro Inhibitory Effects of Antisera to SigA2

Confluent HeLa cells were infected with an invasive S. flexneri 2a 2457T strain at a multiplicity of infection (m.o.j.) of 100, 10, and 1 for 2 hours at 3° C. The bacteria were washed and cultures were overlaid with agarose. Plaques were visualized by Giemsa staining, performed 48 hours after the infection. To test antisera to SigA2 for its capacity to inhibit plaque formation, invasive bacteria and test antiserum were mixed for 20 min prior to being added to the cells (FIGS. 9A-B). Plaque reduction was monitored after Giemsa staining. As can be seen in FIG. 9B, antibodies to SigA2 inhibited plaque formation induced by S. flexneri. At M.O.I 10, the number of plaques induced by invasive S. flexneri 2a in infected cells was reduced by about 60% reduction in the presence of mouse antiserum to SigA2 (FIG. 9B) compare to control without antiserum (FIG. 9A).

Example 12

Confirmation of the Presence of IcsP and SigA in Shigella Strains

The presence of IcsP and SigA in Shigella strains was confirmed by PCR using the primers used for construction of overexpression vectors described in the above section entitled "Cloning, expression and purification of Shigella SigA2 and Icsp2 polypeptides."

Figure 10:
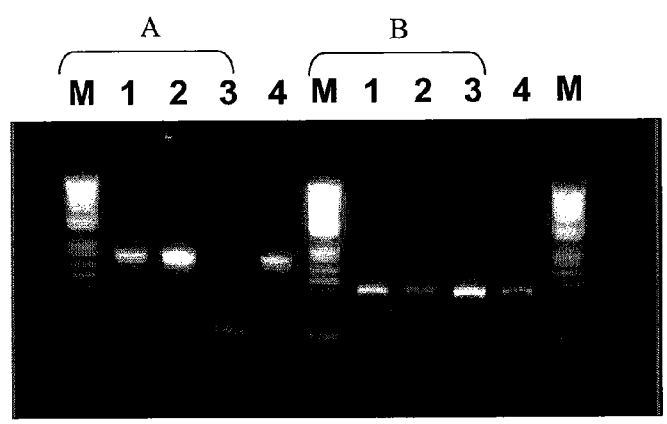
FIG. 10 is photograph of a gel showing the presence of sigA gene and icsP gene in each serotype of *Shigella* spp.

The presence of sigA gene and icsP gene in each serotype of Shigella spp. was confirmed by PCR with primer sets for SigA2 and IcsP2 fragments, as shown in FIG. 10. Nucleic acid fragments of sigA2 and icsP2 were amplified by PCR from all the strains except for sigA in S. dysenteriae, the sigA gene is known to be absent in S. dysenteriae strains by whole genome sequencing results (39).

Example 13

Antibodies Against SigA2 Inhibit Keratoconjunctivitis by S. flexneri 2a

Figures 11, 11A, 11B, 11C, 11D:
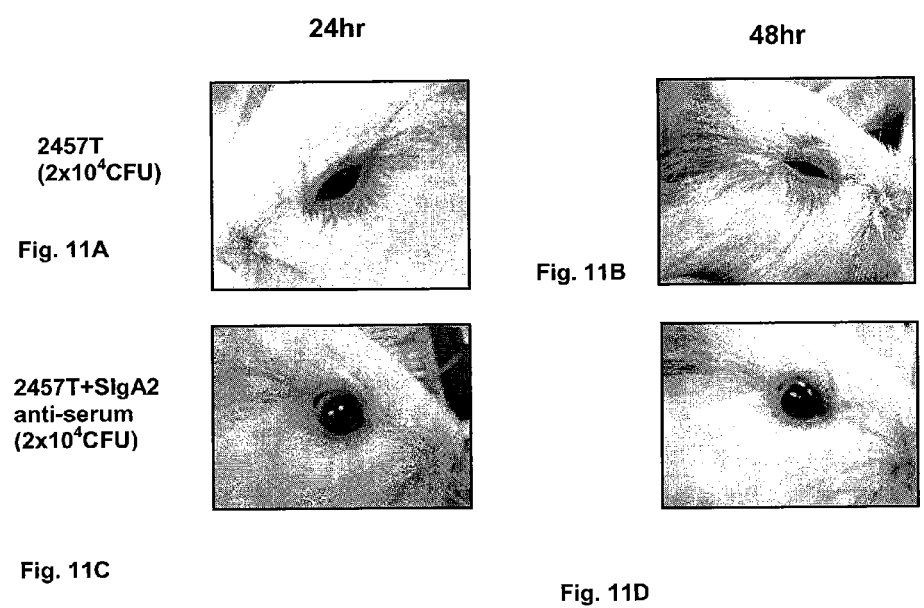

Virulent S. flexneri 2a strain 2457T ($2 \times 10^4$ colony-forming units in 20 microliter) was mixed with PBS, the same volume of antiserum against SigA2, or pre-immune sera, and then inoculated into the conjunctival sac of guinea pigs. As can be seen in FIG. 11A, the upper left panel shows moderate (24 hrs) periocular inflammation in a control animal which becomes severe at 48 hrs (upper right panel, FIG. 11B) after inoculation of S. flexneri 2a (strain 2457T). In contrast, and as can be seen in the bottom two panels of FIG. 11, an antiserum to SIgA2 inhibited ocular inflammation induced by co-administered S. flexneri (strain 2457T) bacteria after 24 hours (FIG. 11C) and after 48 hours (FIG. 11D). Guinea pig inoculated with bacteria mixed with pre-immune serum developed keratoconjunctivitis.

Example 14 icsP and sigA Disrupted Mutant Strains can Escape from Immunities Induced by IcsP2 and SigA2, Respectively Mice were immunized with IcsP2, SigA2 or SC602 (a live-attenuated S. flexneri 2a strain), respectively. Animals were challenged with S. flexneri 2a or with S. flexneri 2a deleted of either IcsP or SigA (herein referred to as KO strains). As shown in Table 4, mice survive a challenge with S. flexneri 2a but succumbed to challenge with KO strains, demonstrating the specificity of protection induced by IcsP2 and SigA2 respectively.

TABLE 4

| | Survival of mice after challenge with virulent strains | | | | | | |
|---|---|---|---|---|---|---|---|
| | S. flexneri 2a | S. flexneri 2a icsP KO strain | S. flexneri 2a sigA KO strain | S. flexneri 5a | S. dysenteriae 1 | S. boydii | S. sonnei |
| IcsP2 | 80% | 0 | 70% | 60% | 60% | 70% | 80% |
| SigA2 | >80% | 80% | 0 | 0 | 0 | 80% | 80% |

TABLE 4-continued

Survival of mice after challenge with virulent strains

| | S. flexneri 2a | S. flexneri 2a icsP KO strain | S. flexneri 2a sigA KO strain | S. flexneri 5a | S. dysenteriae 1 | S. boydii | S. sonnei |
|---|---|---|---|---|---|---|---|
| SC602 (S. flexneri 2a) | 100% | 100% | 100% | 0 | 0 | 0 | 0 |

REFERENCES

1. Al-Hasani, K., K. Rajakumar, D. Bulach, R. Robins-Browne, B. Adler, and H. Sakellaris. 2001. Genetic organization of the she pathogenicity island in *Shigella flexneri* 2a. Microb Pathog 30:1-8.
2. Bernardini, M. L., J. Mounier, H. d'Hauteville, M. Coquis-Rondon, and P. J. Sansonetti. 1989. Identification of icsA, a plasmid locus of *Shigella flexneri* that governs bacterial intra- and intercellular spread through interaction with F-actin. Proc Natl Acad Sci USA 86:3867-71.
3. Buchrieser, C., P. Glaser, C. Rusniok, H. Nedjari, H. D'Hauteville, F. Kunst, P. Sansonetti, and C. Parsot. 2000. The virulence plasmid pWRI00 and the repertoire of proteins secreted by the type III secretion apparatus of *Shigella flexneri*. Mol Microbiol 38:760-71.
4. Czerkinsky, C., Z. Moldoveanu, J. Mestecky, L. A. Nilsson, and O. Ouchterlony. 1988. A novel two colour ELISPOT assay. I. Simultaneous detection of distinct types of antibody-secreting cells. J Immunol Methods 115:31-7.
5. DuPont, H. L., R. B. Hornick, M. J. Snyder, J. P. Libonati, S. B. Formal, and E. J. Gangarosa. 1972. Immunity in shigellosis. II. Protection induced by oral live vaccine or primary infection. J Infect Dis 125: 12-6.
6. DuPont, H. L., M. M. Levine, R. B. Hornick, and S. B. Formal. 1989. Inoculum size in shigellosis and implications for expected mode of transmission. J Infect Dis 159: 1126-8.
7. Fukuda, I., T. Suzuki, H. Munakata, N. Hayashi, E. Katayama, M. Yoshikawa, and C. Sasakawa. 1995. Cleavage of *Shigella* surface protein VirG occurs at a specific site, but the secretion is not essential for intracellular spreading. J Bacteriol 177:1719-26.
8. Girardin, S. E., I. G. Boneca, L. A. Carneiro, A. Antignac, M. Jehanno, J. Viala, K. Tedin, M. K. Taha, A. Labigne, U. Zahringer, A. J. Coyle, P. S. DiStefano, J. Bertin, P. J. Sansonetti, and D. J. Philpott. 2003. NodI detects a unique muropeptide from gram-negative bacterial peptidoglycan. Science 300:1584-7.
9. Goldberg, M. B., O. Barzu, C. Parsot, and P. J. Sansonetti. 1993. Unipolar localization and ATPase activity of IcsA, a *Shigella flexneri* protein involved in intracellular movement. J Bacteriol 175:2189-96.
10. Hartman, A. B., C. J. Powell, C. L. Schultz, E. V. Oaks, and K. H. Eckels. 1991. Small-animal model to measure efficacy and immunogenicity of *Shigella* vaccine strains. Infect Immun 59:4075-83.
11. Hartman, A. B., and M. M. Venkatesan. 1998. Construction of a Stable Attenuated *Shigella sonnei* Δ virG Vaccine Strain, WRSS1, and Protective Efficacy and Immunogenicity in the Guinea Pig Keratoconjunctivitis Model. Infect. Immun. 66:4572-4576.
12. Hoge, C. W., J. M. Gambel, A. Srijan, C. Pitarangsi, and P. Echeverria. 1998. Trends in antibiotic resistance among diarrheal pathogens isolated in Thailand over 15 years. Clin Infect Dis 26:341-5.
13. Jennison, A. V., R. Raqib, and N. K. Verma. 2006. Immunoproteome analysis of soluble and membrane proteins of *Shigella flexneri* 2457T. World J Gastroenterol 12:6683-8.
14. Jiang, Y., F. Yang, X. Zhang, J. Yang, L. Chen, Y. Yan, H. Nie, Z. Xiong, J. Wang, J. Dong, Y. Xue, X. Xu, Y. Zhu, S. Chen, and Q. Jin. 2005. The complete sequence and analysis of the large virulence plasmid pSS of *Shigella sonnei*. Plasmid 54:149-59.
15. Jin, Q., Z. Yuan, J. Xu, Y. Wang, Y. Shen, W. Lu, J. Wang, H. Liu, J. Yang, F. Yang, X. Zhang, J. Zhang, G. Yang, H. Wu, D. Qu, J. Dong, L. Sun, Y. Xue, A. Zhao, Y. Gao, J. Zhu, B. Kan, K. Ding, S. Chen, H. Cheng, Z. Yao, B. He, R. Chen, D. Ma, B. Qiang, Y. Wen, Y. Hou, and J. Yu. 2002. Genome sequence of *Shigella flexneri* 2a: insights into pathogenicity through comparison with genomes of *Escherichia coli* K12 and O157. Nucl. Acids Res. 30:4432-4441.
16. Katz, D. E., T. S. Coster, M. K. Wolf, F. C. Trespalacios, D. Cohen, G. Robins, A. B. Hartman, M. M. Venkatesan, D. N. Taylor, and T. L. Hale. 2004. Two studies evaluating the safety and immunogenicity of a live, attenuated *Shigella flexneri* 2a vaccine (SC602) and excretion of vaccine organisms in North American volunteers. Infect Immun 72:923-30.
17. Kotloff, K. L., M. F. Pasetti, E. M. Barry, J. P. Nataro, S. S. Wasserman, M. B. Sztein, W. D. Picking, and M. M. Levine. 2004. Deletion in the *Shigella* enterotoxin genes further attenuates *Shigella flexneri* 2a bearing guanine auxotrophy in a phase 1 trial of CVD 1204 and CVD 1208. J Infect Dis 190: 1745-54.
18. McKenzie, R., R. I. Walker, G. S, Nabors, L. L. Van De Verg, C. Carpenter, G. Gomes, E. Forbes, J. H. Tian, H. H. Yang, J. L. Pace, W. J. Jackson, and A. L. Bourgeois. 2006. Safety and immunogenicity of an oral, inactivated, whole-cell vaccine for *Shigella sonnei*: preclinical studies and a Phase I trial. Vaccine 24:3735-45.
19. Mukhopadhaya, A., D. Mahalanabis, and M. K. Chakrabarti. 2006. Role of *Shigella flexneri* 2a 34 kDa outer membrane protein in induction of protective immune response. Vaccine 24:6028-36.
20. Nie, H., F. Yang, X. Zhang, J. Yang, L. Chen, J. Wang, Z. Xiong, J. Peng, L. Sun, J. Dong, Y. Xue, X. Xu, S. Chen, Z. Yao, Y. Shen, and Q. Jin. 2006. Complete genome sequence of *Shigella flexneri* 5b and comparison with *Shigella flexneri* 2a. BMC Genomics 7:173.
21. Noriega, F. R., F. M. Liao, D. R. Maneval, S. Ren, S. B. Formal, and M. M. Levine. 1999. Strategy for Cross-Protection among *Shigella flexneri* Serotypes. Infect. Immun. 67:782-788.
22. Noriega, F. R., J. Y. Wang, G. Losonsky, D. R. Maneval, D. M. Hone, and M. M. Levine. 1994. Construction and characterization of attenuated delta aroA delta virG *Shigella flexneri* 2a strain CVD 1203, a prototype live oral vaccine. Infect. Immun. 62:5168-5172.

23. Oaks, E. v., and K. R. Turbyfill. 2006. Development and evaluation of a *Shigella flexneri* 2a and *S. sonnei* bivalent invasion complex (Invaplex) vaccine. Vaccine 24:2290-301.

24. Orr, N., G. Robin, D. Cohen, R. Amon, and G. H. Lowell. 1993. Immunogenicity and efficacy of oral or intranasal *Shigella flexneri* 2a and *Shigella sonnei* proteosome-lipopolysaccharide vaccines in animal models. Infect Immun 61:2390-5.

25. Passwell, J. H., E. Harley, S. Ashkenazi, C. Chu, D. Miron, R. Ramon, N. Farzan, J. Shiloach, D. A. Bryla, F. Majadly, R. Roberson, J. B. Robbins, and R. Schneerson. 2001. Safety and immunogenicity of improved *Shigella* O-specific polysaccharide-protein conjugate vaccines in adults in Israel. Infect Immun 69: 13 51-7.

26. Perdomo, J. J., P. Gounon, and P. J. Sansonetti. 1994. Polymorphonuclear leukocyte transmigration promotes invasion of colonic epithelial monolayer by *Shigella flexneri*. J Clin Invest 93:633-43.

27. Robbins, J. R., D. Monack, S. J. McCallum, A. Vegas, E. Pham, M. B. Goldberg, and J. A. Theriot. 2001. The making of a gradient: IcsA (VirG) polarity in *Shigella flexneri*. Mol Microbio 141:861-72.

28. Sereny, B. 1957. Experimental keratoconjunctivitis shigellosa. Acta Microbiol Acad Sci Hung 4:367-376.

29. Shere, K. D., S. Sallustio, A. Manessis, T. G. D'Aversa, and M. B. Goldberg. 1997. Disruption of IcsP, the major *Shigella* protease that cleaves IcsA, accelerates actin-based motility. Mol Microbio 125:451-62.

30. Shim, D.-H., T. Suzuki, S.-Y. Chang, S.-M. Park, P. J. Sansonetti, C. Sasakawa, and M.-N. Kweon. 2007. New Animal Model of Shigellosis in the Guinea Pig: Its Usefulness for Protective Efficacy Studies. J Immunol 178: 2476-2482.

31. Shim, D. H., S. Y. Chang, S. M. Park, H. Jang, R. Carbis, C. Czerkinsky, S. Uematsu, S. Akira, and M. N. Kweon. 2007. Immunogenicity and protective efficacy offered by a ribosomal-based vaccine from *Shigella flexneri* 2a. Vaccine 25:4828-36.

32. Suzuki, T., M. C. Lett, and C. Sasakawa. 1995. Extracellular transport of VirG protein in *Shigella*. J Biol Chem 270:30874-80.

33. Venkatesan, M. M., A. B. Hartman, J. W. Newland, V. S. Ivanova, T. L. Hale, M. McDonough, and J. Butterton. 2002. Construction, characterization, and animal testing of WRSd1, a *Shigella dysenteriae* 1 vaccine. Infect Immun 70:2950-8.

34. Villavedra, M., H. Carol, M. Hjulstrom, 1. Holmgren, and C. Czerkinsky. 1997. "PERFEXT": a direct method for quantitative assessment of cytokine production in vivo at the local level. Res Immuno 148:257-66.

35. von Seidlein, L., D. R. Kim, M. Ali, H. Lee, X. Wang, V. D. Thiem, G. Canh do, W. Chaicumpa, M. D. Agtini, A. Hossain, Z. A. Bhutta, C. Mason, O, Sethabutr, K. Talukder, G. B. Nair, J. L. Deen, K. Kotloff, and J. Clemens. 2006. A multicentre study of *Shigella* diarrhoea in six Asian countries: disease burden, clinical manifestations, and microbiology. PLoS Med 3:e353.

36. Wei, C., J. Yang, J. Zhu, X. Zhang, W. Leng, J. Wang, Y. Xue, L. Sun, W. Li, J. Wang, and Q. Jin. 2006. Comprehensive proteomic analysis of *Shigella flexneri* 2a membrane proteins. J Proteome Res 5:1860-5.

37. Wei, J., M. B. Goldberg, V. Burland, M. M. Venkatesan, W. Deng, G. Fournier, G. F. Mayhew, G. Plunkett, III, D. J. Rose, A. Darling, B. Mau, N. T. Perna, S. M. Payne, L. J. Runyen-Janecky, S. Zhou, D.C. Schwartz, and F. R. Blattner. 2003. Complete Genome Sequence and Comparative Genomics of *Shigella flexneri* Serotype 2a Strain 2457T. Infect. Immun. 71:2775-2786.

38. Yang, F., J. Yang, X. Zhang, L. Chen, Y. Jiang, Y. Yan, X. Tang, J. Wang, Z. Xiong, J. Dong, Y. Xue, Y. Zhu, X. Xu, L. Sun, S. Chen, H. Nie, J. Peng, J. Xu, Y. Wang, Z. Yuan, Y. Wen, Z. Yao, Y. Shen, B. Qiang, Y. Hou, J. Yu, and Q. Jin. 2005. Genome dynamics and diversity of *Shigella* species, the etiologic agents of bacillary dysentery. Nucleic Acids Res 33:6445-58.

39. Yang, J., L. Chen, J. Yu, L. Sun, and Q. Jin. 2006. ShiBASE: an integrated database for comparative genomics of *Shigella*. Nucleic Acids Res 34:D398-401.

40. Echeverria P, Sethabutr O, Pitarangsi C. Microbiology and diagnosis of infections with *Shigella* and enteroinvasive *Escherichia coli*. Rev Infect Dis. 1991 13 Suppl 4:S220-5. Review.

41. Sethabutr O, Echeverria P, Hoge C W, Bodhidatta L, Pitarangsi C. Detection of *Shigella* and enteroinvasive *Escherichia coli* by PCR in the stools of patients with dysentery in Thailand. J Diarrhoeal Dis Res. 1994 12:265-9.

42. Gu, X., et al., "Synthesis, Characterization, and Immunologic Properties of Detoxified Lipooligosaccharide from Nontypeable *Haemophilus influenza* Conjugated to Proteins", Infection and Immunity, 64 (10), (1996), pp. 4047-4053.

43. Gupta, R., et al., "Comparative Immunogenicity of Conjugates Composed of *Escherichia coli* O1110-Specific Polysaccharide, Prepared by Treatment with Acetic Acid or Hydrazine, Bound to Tetanus Toxoid by Two Synthetic Schemes", *Infection and Immunity*, 63 (8), (1995), pp. 2805-2810.

44. Gupta, R., et al., "Synthesis, Characterization, and Some Immunological Properties of Conjugates Composed of the Detoxified Lipopolysaccharide of *Vibrio cholerae* O1 Serotype Inaba Bound to Cholera Toxin", *Infection and Immunity*, 60 (8), (1992), pp. 3201-3208.

45. Konadu, E., et al., "Investigational Vaccine for *Escherichia coli* O157: Phase 1 Study of O157 O-Specific Polysaccharide-*Pseudomonas aeruginosa* Recombinant Exprotein A Conjugates in Adults", *Journal of Infectious Diseases*, 177, (1998), pp. 383-387.

46. Konadu, E., et al., "Phase 1 and Phase 2 Studies of *Salmonella enterica* Serovar Paratyphi A O-Specific Polysaccharide-Tetanus Toxoid Conjugates in Adults, Teenagers, and 2- to 4-Year Old Children in Vietnam", *Infection and Immunity*, 68 (3), (2000), pp. 1529-1534.

47. Konadu, E., et al., "Preparation, Characterization, and Immunological Properties in Mice of *Escherichia coli* O157 O-Specific Polysaccharide-Protein Conjugate Vaccines", *Infection and Immunity*, 62 (11), (1994), pp. 5048-5054.

48. Robbins, J., et al., "Polysaccharide-Protein Conjugates: A New Generation of Vaccines", The Journal of Infectious Diseases, 161, (1990), pp. 821-832.

49. Taylor, D., et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (Plesiomonas shigelloides) Bound to Bacterial Toxoids", *Infection and Immunity*, 61, (1993), pp. 3678-3687.

50. WO/1999/003871.
51. U.S. Pat. No. 4,771,127
52. U.S. Pat. No. 5,866,132.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A conjugate molecule comprising an O-specific polysaccharide antigen of *Shigella* bacteria covalently bound to the *Shigella* IcsP2 or SigA2 protein.

2. A conjugate molecule comprising a saccharide compound comprising an O antigen of *Shigella* bacteria covalently bound to an isolated polypeptide comprising the amino acid sequence as set forth in SEQ ID NO:2.

3. A vaccine for immunizing a mammal in need thereof against shigellosis comprising the conjugate molecule of claim 1.

4. A conjugate molecule comprising a polysaccharide from a bacteria non related to the genus *Shigella* covalently bound to the *Shigella* IcsP2 or SigA2 protein.

5. A conjugate molecule comprising a polysaccharide from a bacteria non related to the genus *Shigella* covalently bound to an isolated polypeptide comprising the amino acid sequence as set forth in SEQ ID NO:2.

6. The conjugate molecule of claim 5 wherein said polysaccharide is lipopolysaccharide.

7. A vaccine for immunizing a mammal in need thereof against shigellosis comprising the conjugate molecule of claim 4.

8. A vaccine for immunizing a mammal in need thereof against shigellosis comprising the conjugate molecule of claim 2.

9. A vaccine for immunizing a mammal in need thereof against shigellosis and a disease caused by *Shigella*, wherein the vaccine comprises the conjugate of claim 4.

10. A vaccine for immunizing a mammal in need thereof against shigellosis and a disease caused by *Shigella*, wherein the vaccine comprises the conjugate of claim 5.

* * * * *

```
                        SEQUENCE LISTING

<160> NUMBER OF SEQ ID NOS: 24

<210> SEQ ID NO 1
<211> LENGTH: 390
<212> TYPE: DNA
<213> ORGANISM: Shigella flexneri
<220> FEATURE:
<221> NAME/KEY: CDS
<222> LOCATION: (1)..(390)

<400> SEQUENCE: 1 agt gaa aac ggg ggg agc agg aat aaa aaa ggg gca cat cct agt ggt      48
Ser Glu Asn Gly Gly Ser Arg Asn Lys Lys Gly Ala His Pro Ser Gly
1               5                   10                  15 gaa aga aca ata ggt tac aaa cag ctc ttc aaa ata cct tat att gga      96
Glu Arg Thr Ile Gly Tyr Lys Gln Leu Phe Lys Ile Pro Tyr Ile Gly
            20                  25                  30 tta act gct aat tac cgc cat gag aat ttt gag ttt gga gca gaa ctg     144
Leu Thr Ala Asn Tyr Arg His Glu Asn Phe Glu Phe Gly Ala Glu Leu
        35                  40                  45 aaa tat agt ggt tgg gtt ctt tca tct gat aca gat aaa cac tat cag     192
Lys Tyr Ser Gly Trp Val Leu Ser Ser Asp Thr Asp Lys His Tyr Gln
    50                  55                  60 act gag aca att ttt aaa gat gaa ata aaa aac caa aat tac tgc tct     240
Thr Glu Thr Ile Phe Lys Asp Glu Ile Lys Asn Gln Asn Tyr Cys Ser
65                  70                  75                  80 gtt gct gcg aat att gga tac tat gtc acc ccc agt gca aaa ttt tat     288
Val Ala Ala Asn Ile Gly Tyr Tyr Val Thr Pro Ser Ala Lys Phe Tyr
                85                  90                  95 ata gaa ggc tcc aga aat tac att tct aat aaa aaa ggt gat aca tct     336
Ile Glu Gly Ser Arg Asn Tyr Ile Ser Asn Lys Lys Gly Asp Thr Ser
            100                 105                 110 ctt tat gag caa agt acc aat ata tct ggc acc att aaa aat agt gca     384
Leu Tyr Glu Gln Ser Thr Asn Ile Ser Gly Thr Ile Lys Asn Ser Ala
        115                 120                 125 agt att                                                            390
Ser Ile
    130

<210> SEQ ID NO 2
<211> LENGTH: 130
<212> TYPE: PRT
<213> ORGANISM: Shigella flexneri

<400> SEQUENCE: 2

Ser Glu Asn Gly Gly Ser Arg Asn Lys Lys Gly Ala His Pro Ser Gly
1               5                   10                  15

Glu Arg Thr Ile Gly Tyr Lys Gln Leu Phe Lys Ile Pro Tyr Ile Gly
            20                  25                  30

Leu Thr Ala Asn Tyr Arg His Glu Asn Phe Glu Phe Gly Ala Glu Leu
        35                  40                  45

Lys Tyr Ser Gly Trp Val Leu Ser Ser Asp Thr Asp Lys His Tyr Gln
    50                  55                  60

Thr Glu Thr Ile Phe Lys Asp Glu Ile Lys Asn Gln Asn Tyr Cys Ser
65                  70                  75                  80
```

```
Val Ala Ala Asn Ile Gly Tyr Tyr Val Thr Pro Ser Ala Lys Phe Tyr
                85                  90                  95

Ile Glu Gly Ser Arg Asn Tyr Ile Ser Asn Lys Lys Gly Asp Thr Ser
            100                 105                 110

Leu Tyr Glu Gln Ser Thr Asn Ile Ser Gly Thr Ile Lys Asn Ser Ala
        115                 120                 125

Ser Ile
    130

<210> SEQ ID NO 3
<211> LENGTH: 795
<212> TYPE: DNA
<213> ORGANISM: Shigella flexneri
<220> FEATURE:
<221> NAME/KEY: CDS
<222> LOCATION: (1)..(795)

<400> SEQUENCE: 3 gaa aaa gcc ttc aat aaa att tac atg gcc gga ggt aaa ggt acg gta    48
Glu Lys Ala Phe Asn Lys Ile Tyr Met Ala Gly Gly Lys Gly Thr Val
1               5                   10                  15 aaa ata aat gcc aaa gac gct tta agc gaa agc ggt aat ggc gaa atc    96
Lys Ile Asn Ala Lys Asp Ala Leu Ser Glu Ser Gly Asn Gly Glu Ile
            20                  25                  30 tat ttt acc aga aat ggc gga aca ctg gat cta aac ggc tat gac cag   144
Tyr Phe Thr Arg Asn Gly Gly Thr Leu Asp Leu Asn Gly Tyr Asp Gln
        35                  40                  45 tca ttt cag aaa atc gca gca aca gat gcg gga aca acc gta acg aac   192
Ser Phe Gln Lys Ile Ala Ala Thr Asp Ala Gly Thr Thr Val Thr Asn
    50                  55                  60 tca aac gtg aag caa tca aca tta tca ctt act aat act gat gca tat   240
Ser Asn Val Lys Gln Ser Thr Leu Ser Leu Thr Asn Thr Asp Ala Tyr
65                  70                  75                  80 atg tac cat ggg aat gta tca ggt aat ata agc ata aat cat att atc   288
Met Tyr His Gly Asn Val Ser Gly Asn Ile Ser Ile Asn His Ile Ile
                85                  90                  95 aat act acc cag caa cat aac aat aat gcc aat ctg atc ttt gat ggc   336
Asn Thr Thr Gln Gln His Asn Asn Asn Ala Asn Leu Ile Phe Asp Gly
            100                 105                 110 tca gtc gat atc aaa aac gat atc tct gtc cgg aat gca cag tta aca   384
Ser Val Asp Ile Lys Asn Asp Ile Ser Val Arg Asn Ala Gln Leu Thr
        115                 120                 125 tta caa gga cat gcg aca gaa cat gcc ata ttt aaa gaa ggc aat aac   432
Leu Gln Gly His Ala Thr Glu His Ala Ile Phe Lys Glu Gly Asn Asn
    130                 135                 140 aac tgt cca att cct ttt tta tgt caa aaa gac tat tct gct gcc ata   480
Asn Cys Pro Ile Pro Phe Leu Cys Gln Lys Asp Tyr Ser Ala Ala Ile
145                 150                 155                 160 aag gac cag gaa agc act gta aat aaa cgt tac aat acg gaa tat aag   528
Lys Asp Gln Glu Ser Thr Val Asn Lys Arg Tyr Asn Thr Glu Tyr Lys
                165                 170                 175 tcc aac aat cag ata gcc tct ttt tcc cag ccc gac tgg gaa agt cgt   576
Ser Asn Asn Gln Ile Ala Ser Phe Ser Gln Pro Asp Trp Glu Ser Arg
            180                 185                 190 aaa ttt aat ttc cgg aaa tta aat tta gaa aac gca acc ctg agt ata   624
Lys Phe Asn Phe Arg Lys Leu Asn Leu Glu Asn Ala Thr Leu Ser Ile
        195                 200                 205 ggc cgg gat gct aat gta aaa gga cac ata gag gct aaa aac tct caa   672
Gly Arg Asp Ala Asn Val Lys Gly His Ile Glu Ala Lys Asn Ser Gln
    210                 215                 220 att gtt ctg gga aat aaa act gca tac att gac atg ttc tca gga aga   720
Ile Val Leu Gly Asn Lys Thr Ala Tyr Ile Asp Met Phe Ser Gly Arg
```

```
Ile Val Leu Gly Asn Lys Thr Ala Tyr Ile Asp Met Phe Ser Gly Arg
225                 230                 235                 240 aac att act ggc gaa ggt ttt gga ttc aga caa cag ctt cgc tcc ggg        768
Asn Ile Thr Gly Glu Gly Phe Gly Phe Arg Gln Gln Leu Arg Ser Gly
                245                 250                 255 gat tca gca ggc gaa agt agt ttc aac                                    795
Asp Ser Ala Gly Glu Ser Ser Phe Asn
                260                 265
```

<210> SEQ ID NO 4
<211> LENGTH: 265
<212> TYPE: PRT
<213> ORGANISM: Shigella flexneri

<400> SEQUENCE: 4

```
Glu Lys Ala Phe Asn Lys Ile Tyr Met Ala Gly Gly Lys Gly Thr Val
1               5                   10                  15

Lys Ile Asn Ala Lys Asp Ala Leu Ser Glu Ser Gly Asn Gly Glu Ile
            20                  25                  30

Tyr Phe Thr Arg Asn Gly Gly Thr Leu Asp Leu Asn Gly Tyr Asp Gln
        35                  40                  45

Ser Phe Gln Lys Ile Ala Ala Thr Asp Ala Gly Thr Thr Val Thr Asn
50                  55                  60

Ser Asn Val Lys Gln Ser Thr Leu Ser Leu Thr Asn Thr Asp Ala Tyr
65                  70                  75                  80

Met Tyr His Gly Asn Val Ser Gly Asn Ile Ser Ile Asn His Ile Ile
                85                  90                  95

Asn Thr Thr Gln Gln His Asn Asn Ala Asn Leu Ile Phe Asp Gly
            100                 105                 110

Ser Val Asp Ile Lys Asn Asp Ile Ser Val Arg Asn Ala Gln Leu Thr
        115                 120                 125

Leu Gln Gly His Ala Thr Glu His Ala Ile Phe Lys Glu Gly Asn Asn
130                 135                 140

Asn Cys Pro Ile Pro Phe Leu Cys Gln Lys Asp Tyr Ser Ala Ala Ile
145                 150                 155                 160

Lys Asp Gln Glu Ser Thr Val Asn Lys Arg Tyr Asn Thr Glu Tyr Lys
                165                 170                 175

Ser Asn Asn Gln Ile Ala Ser Phe Ser Gln Pro Asp Trp Glu Ser Arg
            180                 185                 190

Lys Phe Asn Phe Arg Lys Leu Asn Leu Glu Asn Ala Thr Leu Ser Ile
        195                 200                 205

Gly Arg Asp Ala Asn Val Lys Gly His Ile Glu Ala Lys Asn Ser Gln
210                 215                 220

Ile Val Leu Gly Asn Lys Thr Ala Tyr Ile Asp Met Phe Ser Gly Arg
225                 230                 235                 240

Asn Ile Thr Gly Glu Gly Phe Gly Phe Arg Gln Gln Leu Arg Ser Gly
                245                 250                 255

Asp Ser Ala Gly Glu Ser Ser Phe Asn
                260                 265
```

<210> SEQ ID NO 5
<211> LENGTH: 948
<212> TYPE: DNA
<213> ORGANISM: Shigella flexneri
<220> FEATURE:
<221> NAME/KEY: CDS
<222> LOCATION: (1)..(945)

<400> SEQUENCE: 5

```
atg aaa tta aaa ttc ttt gta ctt gca ctt tgt gta cct gcg atc ttt     48
Met Lys Leu Lys Phe Phe Val Leu Ala Leu Cys Val Pro Ala Ile Phe
1               5                   10                  15 act aca cat gct acc act aac tat cca ctt ttc ata ccg gac aac atc     96
Thr Thr His Ala Thr Thr Asn Tyr Pro Leu Phe Ile Pro Asp Asn Ile
                20                  25                  30 agt acg gat att agt cta gga tct ctg agt ggc aaa aca aaa gaa cgc    144
Ser Thr Asp Ile Ser Leu Gly Ser Leu Ser Gly Lys Thr Lys Glu Arg
            35                  40                  45 gtt tat cat ccc aag gaa ggg ggg aga aaa att agt caa ctg gac tgg    192
Val Tyr His Pro Lys Glu Gly Gly Arg Lys Ile Ser Gln Leu Asp Trp
        50                  55                  60 aaa tac agt aat gcg act att gtt aga ggt ggc atc gat tgg aag cta    240
Lys Tyr Ser Asn Ala Thr Ile Val Arg Gly Gly Ile Asp Trp Lys Leu
65                  70                  75                  80 att cca aaa gtg tct ttc gga gtt tcc ggt tgg act act tta ggt aac    288
Ile Pro Lys Val Ser Phe Gly Val Ser Gly Trp Thr Thr Leu Gly Asn
                85                  90                  95 cag aaa gca agc atg gtt gat aaa gac tgg aac aat tcc aat acc cct    336
Gln Lys Ala Ser Met Val Asp Lys Asp Trp Asn Asn Ser Asn Thr Pro
            100                 105                 110 cag gta tgg acc gac cag agc tgg cat ccc aat acg cat ctc cgt gat    384
Gln Val Trp Thr Asp Gln Ser Trp His Pro Asn Thr His Leu Arg Asp
        115                 120                 125 gct aac gaa ttc gag ctg aat ctt aaa ggt tgg tta tta aat aat ttg    432
Ala Asn Glu Phe Glu Leu Asn Leu Lys Gly Trp Leu Leu Asn Asn Leu
    130                 135                 140 gat tat cga ctt gga cta ata gca ggt tac caa gag agt cgt tac agt    480
Asp Tyr Arg Leu Gly Leu Ile Ala Gly Tyr Gln Glu Ser Arg Tyr Ser
145                 150                 155                 160 ttt aat gca atg gga ggg agt tat att tat agt gaa aac ggg ggg agc    528
Phe Asn Ala Met Gly Gly Ser Tyr Ile Tyr Ser Glu Asn Gly Gly Ser
                165                 170                 175 agg aat aaa aaa ggg gca cat cct agt ggt gaa aga aca ata ggt tac    576
Arg Asn Lys Lys Gly Ala His Pro Ser Gly Glu Arg Thr Ile Gly Tyr
            180                 185                 190 aaa cag ctc ttc aaa ata cct tat att gga tta act gct aat tac cgc    624
Lys Gln Leu Phe Lys Ile Pro Tyr Ile Gly Leu Thr Ala Asn Tyr Arg
        195                 200                 205 cat gag aat ttt gag ttt gga gca gaa ctg aaa tat agt ggt tgg gtt    672
His Glu Asn Phe Glu Phe Gly Ala Glu Leu Lys Tyr Ser Gly Trp Val
    210                 215                 220 ctt tca tct gat aca gat aaa cac tat cag act gag aca att ttt aaa    720
Leu Ser Ser Asp Thr Asp Lys His Tyr Gln Thr Glu Thr Ile Phe Lys
225                 230                 235                 240 gat gaa ata aaa aac caa aat tac tgc tct gtt gct gcg aat att gga    768
Asp Glu Ile Lys Asn Gln Asn Tyr Cys Ser Val Ala Ala Asn Ile Gly
                245                 250                 255 tac tat gtc acc ccc agt gca aaa ttt tat ata gaa ggc tcc aga aat    816
Tyr Tyr Val Thr Pro Ser Ala Lys Phe Tyr Ile Glu Gly Ser Arg Asn
            260                 265                 270 tac att tct aat aaa aaa ggt gat aca tct ctt tat gag caa agt acc    864
Tyr Ile Ser Asn Lys Lys Gly Asp Thr Ser Leu Tyr Glu Gln Ser Thr
        275                 280                 285 aat ata tct ggc acc att aaa aat agt gca agt att gaa tat att ggt    912
Asn Ile Ser Gly Thr Ile Lys Asn Ser Ala Ser Ile Glu Tyr Ile Gly
    290                 295                 300 ttt ctc act tcc gca ggt ata aag tat att ttt tga                    948
Phe Leu Thr Ser Ala Gly Ile Lys Tyr Ile Phe
305                 310                 315
```

<210> SEQ ID NO 6
<211> LENGTH: 315
<212> TYPE: PRT
<213> ORGANISM: Shigella flexneri

<400> SEQUENCE: 6

```
Met Lys Leu Lys Phe Phe Val Leu Ala Leu Cys Val Pro Ala Ile Phe
1               5                   10                  15

Thr Thr His Ala Thr Thr Asn Tyr Pro Leu Phe Ile Pro Asp Asn Ile
            20                  25                  30

Ser Thr Asp Ile Ser Leu Gly Ser Leu Ser Gly Lys Thr Lys Glu Arg
        35                  40                  45

Val Tyr His Pro Lys Glu Gly Arg Lys Ile Ser Gln Leu Asp Trp
50                  55                  60

Lys Tyr Ser Asn Ala Thr Ile Val Arg Gly Gly Ile Asp Trp Lys Leu
65                  70                  75                  80

Ile Pro Lys Val Ser Phe Gly Val Ser Gly Trp Thr Thr Leu Gly Asn
                85                  90                  95

Gln Lys Ala Ser Met Val Asp Lys Asp Trp Asn Asn Ser Asn Thr Pro
            100                 105                 110

Gln Val Trp Thr Asp Gln Ser Trp His Pro Asn Thr His Leu Arg Asp
        115                 120                 125

Ala Asn Glu Phe Glu Leu Asn Leu Lys Gly Trp Leu Leu Asn Asn Leu
    130                 135                 140

Asp Tyr Arg Leu Gly Leu Ile Ala Gly Tyr Gln Glu Ser Arg Tyr Ser
145                 150                 155                 160

Phe Asn Ala Met Gly Gly Ser Tyr Ile Tyr Ser Glu Asn Gly Gly Ser
                165                 170                 175

Arg Asn Lys Lys Gly Ala His Pro Ser Gly Glu Arg Thr Ile Gly Tyr
            180                 185                 190

Lys Gln Leu Phe Lys Ile Pro Tyr Ile Gly Leu Thr Ala Asn Tyr Arg
        195                 200                 205

His Glu Asn Phe Glu Phe Gly Ala Glu Leu Lys Tyr Ser Gly Trp Val
    210                 215                 220

Leu Ser Ser Asp Thr Asp Lys His Tyr Gln Thr Glu Thr Ile Phe Lys
225                 230                 235                 240

Asp Glu Ile Lys Asn Gln Asn Tyr Cys Ser Val Ala Ala Asn Ile Gly
                245                 250                 255

Tyr Tyr Val Thr Pro Ser Ala Lys Phe Tyr Ile Glu Gly Ser Arg Asn
            260                 265                 270

Tyr Ile Ser Asn Lys Lys Gly Asp Thr Ser Leu Tyr Glu Gln Ser Thr
        275                 280                 285

Asn Ile Ser Gly Thr Ile Lys Asn Ser Ala Ser Ile Glu Tyr Ile Gly
    290                 295                 300

Phe Leu Thr Ser Ala Gly Ile Lys Tyr Ile Phe
305                 310                 315
```

<210> SEQ ID NO 7
<211> LENGTH: 3858
<212> TYPE: DNA
<213> ORGANISM: Shigella flexneri
<220> FEATURE:
<221> NAME/KEY: CDS
<222> LOCATION: (1)..(3855)

<400> SEQUENCE: 7

```
atg aat aaa att tat tca ctg aaa tat agt cat att aca ggt gga tta      48
Met Asn Lys Ile Tyr Ser Leu Lys Tyr Ser His Ile Thr Gly Gly Leu
1               5                   10                  15 gtt gct gtt tct gaa ctg acc cgg aaa gtt agt gtc ggt aca tca aga      96
Val Ala Val Ser Glu Leu Thr Arg Lys Val Ser Val Gly Thr Ser Arg
            20                  25                  30 aag aaa gtt atc ctc ggt att att tta tcc tca ata tat gga agt tat     144
Lys Lys Val Ile Leu Gly Ile Ile Leu Ser Ser Ile Tyr Gly Ser Tyr
        35                  40                  45 ggc gaa aca gca ttt gca gca atg ctg gat ata aat aat ata tgg acc     192
Gly Glu Thr Ala Phe Ala Ala Met Leu Asp Ile Asn Asn Ile Trp Thr
50                  55                  60 cgc gat tat ctt gac ctt gct caa aac aga gga gag ttc aga ccg ggt     240
Arg Asp Tyr Leu Asp Leu Ala Gln Asn Arg Gly Glu Phe Arg Pro Gly
65                  70                  75                  80 gca aca aat gtt caa tta atg atg aaa gat gga aag ata ttt cat ttt     288
Ala Thr Asn Val Gln Leu Met Met Lys Asp Gly Lys Ile Phe His Phe
                85                  90                  95 cca gaa cta cct gta cct gat ttt tct gct gtt tcc aac aaa ggt gca     336
Pro Glu Leu Pro Val Pro Asp Phe Ser Ala Val Ser Asn Lys Gly Ala
            100                 105                 110 aca aca tca att gga ggt gcg tac agt gtt act gcg act cat aac ggt     384
Thr Thr Ser Ile Gly Gly Ala Tyr Ser Val Thr Ala Thr His Asn Gly
        115                 120                 125 aca cag cat cat gca ata aca aca cag tca tgg gat cag aca gca tat     432
Thr Gln His His Ala Ile Thr Thr Gln Ser Trp Asp Gln Thr Ala Tyr
130                 135                 140 aaa gca agt aac aga gta tca tct ggc gac ttt tcg gtt cat cgt ctg     480
Lys Ala Ser Asn Arg Val Ser Ser Gly Asp Phe Ser Val His Arg Leu
145                 150                 155                 160 aat aaa ttc gtc gtg gaa aca aca ggg gtt acg gag agt gcc gac ttc     528
Asn Lys Phe Val Val Glu Thr Thr Gly Val Thr Glu Ser Ala Asp Phe
                165                 170                 175 tca ctt tct ccc gaa gat gcg atg aaa aga tat ggc gta aac tac aac     576
Ser Leu Ser Pro Glu Asp Ala Met Lys Arg Tyr Gly Val Asn Tyr Asn
            180                 185                 190 ggt aag gaa caa ata att ggc ttc aga gca ggt gcc gga aca acc tca     624
Gly Lys Glu Gln Ile Ile Gly Phe Arg Ala Gly Ala Gly Thr Thr Ser
        195                 200                 205 acg ata tta aac ggc aaa caa tat ctg ttt gga caa aac tat aat ccc     672
Thr Ile Leu Asn Gly Lys Gln Tyr Leu Phe Gly Gln Asn Tyr Asn Pro
210                 215                 220 gac ttg tta agc gca agt ctt ttt aat ctg gac tgg aaa aac aag agt     720
Asp Leu Leu Ser Ala Ser Leu Phe Asn Leu Asp Trp Lys Asn Lys Ser
225                 230                 235                 240 tac att tat acc aac aga acc cct ttt aaa aac tca cca att ttt ggc     768
Tyr Ile Tyr Thr Asn Arg Thr Pro Phe Lys Asn Ser Pro Ile Phe Gly
                245                 250                 255 gat agt ggt tct ggt tct tat cta tat gat aaa gaa caa caa aaa tgg     816
Asp Ser Gly Ser Gly Ser Tyr Leu Tyr Asp Lys Glu Gln Gln Lys Trp
            260                 265                 270 gtt ttc cat ggt gtt acc agt aca gtt ggt ttt atc agt agt acc aat     864
Val Phe His Gly Val Thr Ser Thr Val Gly Phe Ile Ser Ser Thr Asn
        275                 280                 285 ata gcc tgg aca aac tac tcg tta ttt aat aat att ctg gta aac aat     912
Ile Ala Trp Thr Asn Tyr Ser Leu Phe Asn Asn Ile Leu Val Asn Asn
290                 295                 300 tta aaa aag aat ttc aca aac act atg cag ctg gat ggt aaa aaa caa     960
Leu Lys Lys Asn Phe Thr Asn Thr Met Gln Leu Asp Gly Lys Lys Gln
305                 310                 315                 320
```

```
gag tta tca tcg att ata aaa gat aag gac ctg tct gtc tca gga gga       1008
Glu Leu Ser Ser Ile Ile Lys Asp Lys Asp Leu Ser Val Ser Gly Gly
            325                 330                 335 ggg gta tta acg ctc aag cag gat acc gat ctt ggc att ggc ggg ctt       1056
Gly Val Leu Thr Leu Lys Gln Asp Thr Asp Leu Gly Ile Gly Gly Leu
            340                 345                 350 ata ttc gat aag aac cag aca tat aaa gtg tac gga aaa gat aag tct       1104
Ile Phe Asp Lys Asn Gln Thr Tyr Lys Val Tyr Gly Lys Asp Lys Ser
            355                 360                 365 tat aaa ggt gcc ggg ata gat att gat aat aat acc acc gtt gaa tgg       1152
Tyr Lys Gly Ala Gly Ile Asp Ile Asp Asn Asn Thr Thr Val Glu Trp
370                 375                 380 aat gtt aag ggc gtt gcc gga gat aat ctg cat aaa ata ggt agt ggt       1200
Asn Val Lys Gly Val Ala Gly Asp Asn Leu His Lys Ile Gly Ser Gly
385                 390                 395                 400 act ctg gat gta aaa ata gca cag gga aat aac ctt aaa ata ggt aat       1248
Thr Leu Asp Val Lys Ile Ala Gln Gly Asn Asn Leu Lys Ile Gly Asn
            405                 410                 415 ggg act gtc atc ctt agt gct gaa aaa gcc ttc aat aaa att tac atg       1296
Gly Thr Val Ile Leu Ser Ala Glu Lys Ala Phe Asn Lys Ile Tyr Met
            420                 425                 430 gcc gga ggt aaa ggt acg gta aaa ata aat gcc aaa gac gct tta agc       1344
Ala Gly Gly Lys Gly Thr Val Lys Ile Asn Ala Lys Asp Ala Leu Ser
            435                 440                 445 gaa agc ggt aat ggc gaa atc tat ttt acc aga aat ggc gga aca ctg       1392
Glu Ser Gly Asn Gly Glu Ile Tyr Phe Thr Arg Asn Gly Gly Thr Leu
            450                 455                 460 gat cta aac ggc tat gac cag tca ttt cag aaa atc gca gca aca gat       1440
Asp Leu Asn Gly Tyr Asp Gln Ser Phe Gln Lys Ile Ala Ala Thr Asp
465                 470                 475                 480 gcg gga aca acc gta acg aac tca aac gtg aag caa tca aca tta tca       1488
Ala Gly Thr Thr Val Thr Asn Ser Asn Val Lys Gln Ser Thr Leu Ser
            485                 490                 495 ctt act aat act gat gca tat atg tac cat ggg aat gta tca ggt aat       1536
Leu Thr Asn Thr Asp Ala Tyr Met Tyr His Gly Asn Val Ser Gly Asn
            500                 505                 510 ata agc ata aat cat att atc aat act acc cag caa cat aac aat aat       1584
Ile Ser Ile Asn His Ile Ile Asn Thr Thr Gln Gln His Asn Asn Asn
            515                 520                 525 gcc aat ctg atc ttt gat ggc tca gtc gat atc aaa aac gat atc tct       1632
Ala Asn Leu Ile Phe Asp Gly Ser Val Asp Ile Lys Asn Asp Ile Ser
530                 535                 540 gtc cgg aat gca cag tta aca tta caa gga cat gcg aca gaa cat gcc       1680
Val Arg Asn Ala Gln Leu Thr Leu Gln Gly His Ala Thr Glu His Ala
545                 550                 555                 560 ata ttt aaa gaa ggc aat aac aac tgt cca att cct ttt tta tgt caa       1728
Ile Phe Lys Glu Gly Asn Asn Asn Cys Pro Ile Pro Phe Leu Cys Gln
            565                 570                 575 aaa gac tat tct gct gcc ata aag gac cag gaa agc act gta aat aaa       1776
Lys Asp Tyr Ser Ala Ala Ile Lys Asp Gln Glu Ser Thr Val Asn Lys
            580                 585                 590 cgt tac aat acg gaa tat aag tcc aac aat cag ata gcc tct ttt tcc       1824
Arg Tyr Asn Thr Glu Tyr Lys Ser Asn Asn Gln Ile Ala Ser Phe Ser
            595                 600                 605 cag ccc gac tgg gaa agt cgt aaa ttt aat ttc cgg aaa tta aat tta       1872
Gln Pro Asp Trp Glu Ser Arg Lys Phe Asn Phe Arg Lys Leu Asn Leu
            610                 615                 620 gaa aac gca acc ctg agt ata ggc cgg gat gct aat gta aaa gga cac       1920
Glu Asn Ala Thr Leu Ser Ile Gly Arg Asp Ala Asn Val Lys Gly His
625                 630                 635                 640
```

```
ata gag gct aaa aac tct caa att gtt ctg gga aat aaa act gca tac    1968
Ile Glu Ala Lys Asn Ser Gln Ile Val Leu Gly Asn Lys Thr Ala Tyr
            645                 650                 655 att gac atg ttc tca gga aga aac att act ggc gaa ggt ttt gga ttc    2016
Ile Asp Met Phe Ser Gly Arg Asn Ile Thr Gly Glu Gly Phe Gly Phe
        660                 665                 670 aga caa cag ctt cgc tcc ggg gat tca gca ggc gaa agt agt ttc aac    2064
Arg Gln Gln Leu Arg Ser Gly Asp Ser Ala Gly Glu Ser Ser Phe Asn
    675                 680                 685 ggc agt ctg agt gct caa aac agc aaa ata act gtt ggt gat aaa tca    2112
Gly Ser Leu Ser Ala Gln Asn Ser Lys Ile Thr Val Gly Asp Lys Ser
690                 695                 700 act gtt act atg act ggt gca tta tcc tta att aat aca gac ctg att    2160
Thr Val Thr Met Thr Gly Ala Leu Ser Leu Ile Asn Thr Asp Leu Ile
705                 710                 715                 720 atc aac aaa gga gct act gtt acc gcc cag gga aaa atg tat gta gat    2208
Ile Asn Lys Gly Ala Thr Val Thr Ala Gln Gly Lys Met Tyr Val Asp
                725                 730                 735 aaa gct att gaa ctg gcc gga acc ctg aca tta aca ggc acc cct aca    2256
Lys Ala Ile Glu Leu Ala Gly Thr Leu Thr Leu Thr Gly Thr Pro Thr
            740                 745                 750 gaa aat aat aaa tac agc ccg gca atc tat atg tca gat gga tat aat    2304
Glu Asn Asn Lys Tyr Ser Pro Ala Ile Tyr Met Ser Asp Gly Tyr Asn
        755                 760                 765 atg aca gaa gat ggt gcc acg tta aag gct caa aat tat gcc tgg gtc    2352
Met Thr Glu Asp Gly Ala Thr Leu Lys Ala Gln Asn Tyr Ala Trp Val
    770                 775                 780 aat ggt aat ata aaa tca gac aaa aaa gca tct att ctg ttt ggt gtt    2400
Asn Gly Asn Ile Lys Ser Asp Lys Lys Ala Ser Ile Leu Phe Gly Val
785                 790                 795                 800 gac cag tat aaa gaa gat aac ctg gac aaa acc aca cac aca ccg ctg    2448
Asp Gln Tyr Lys Glu Asp Asn Leu Asp Lys Thr Thr His Thr Pro Leu
                805                 810                 815 gct aca ggt ttg ctg ggt ggc ttt gat act tct tat acc gga ggt att    2496
Ala Thr Gly Leu Leu Gly Gly Phe Asp Thr Ser Tyr Thr Gly Gly Ile
            820                 825                 830 gat gct cct gca gcc tca gcc agc atg tat aac acc tta tgg aga gta    2544
Asp Ala Pro Ala Ala Ser Ala Ser Met Tyr Asn Thr Leu Trp Arg Val
        835                 840                 845 aac gga cag tca gcc ctg caa tca tta aaa acc cgc gac agt ctt ttg    2592
Asn Gly Gln Ser Ala Leu Gln Ser Leu Lys Thr Arg Asp Ser Leu Leu
    850                 855                 860 ttg ttt agt aac ata gag aat tcg ggt ttc cat act gtg aca gta aac    2640
Leu Phe Ser Asn Ile Glu Asn Ser Gly Phe His Thr Val Thr Val Asn
865                 870                 875                 880 aca ctg gat gcc act aat act gct gtg att atg cgg gct gat ctg agc    2688
Thr Leu Asp Ala Thr Asn Thr Ala Val Ile Met Arg Ala Asp Leu Ser
                885                 890                 895 cag tct gta aat caa tcg gat aaa ctc att gtt aaa aat cag tta acc    2736
Gln Ser Val Asn Gln Ser Asp Lys Leu Ile Val Lys Asn Gln Leu Thr
            900                 905                 910 gga agc aat aac agt ctg tcg gtc gat ata cag aaa gtg gga aat aat    2784
Gly Ser Asn Asn Ser Leu Ser Val Asp Ile Gln Lys Val Gly Asn Asn
        915                 920                 925 aac tca gga tta aac gtt gac ctg ata aca gcc cca aaa gga agc aat    2832
Asn Ser Gly Leu Asn Val Asp Leu Ile Thr Ala Pro Lys Gly Ser Asn
    930                 935                 940 aaa gag ata ttt aaa gcc agt act cag gcc ata ggt ttc agc aac ata    2880
Lys Glu Ile Phe Lys Ala Ser Thr Gln Ala Ile Gly Phe Ser Asn Ile
945                 950                 955                 960
```

```
tct cct gtg atc agc acg aaa gag gat cag gaa cat acc acg tgg acc    2928
Ser Pro Val Ile Ser Thr Lys Glu Asp Gln Glu His Thr Thr Trp Thr
            965                 970                 975 ctg acc gga tat aag gtg gct gaa aat aca gca tct tcc ggt gca gca    2976
Leu Thr Gly Tyr Lys Val Ala Glu Asn Thr Ala Ser Ser Gly Ala Ala
        980                 985                 990 aaa tcg tat atg tcc ggt aat tac aaa gcc ttc ctg aca gaa gtc aac    3024
Lys Ser Tyr Met Ser Gly Asn Tyr Lys Ala Phe Leu Thr Glu Val Asn
        995                 1000                1005 aac ctg aat aaa cga atg ggg gat ctg cgt gac acc aat ggc gag        3069
Asn Leu Asn Lys Arg Met Gly Asp Leu Arg Asp Thr Asn Gly Glu
    1010                1015                1020 gcc ggt gca tgg gcc cgc atc atg agc gga gca ggt tca gct tct        3114
Ala Gly Ala Trp Ala Arg Ile Met Ser Gly Ala Gly Ser Ala Ser
    1025                1030                1035 ggt gga tac agt gac aac tac acc cat gtg cag att ggt gtg gat        3159
Gly Gly Tyr Ser Asp Asn Tyr Thr His Val Gln Ile Gly Val Asp
    1040                1045                1050 aaa aaa cat gag ctg gat gga ctt gac ctt ttc act ggt ctg act        3204
Lys Lys His Glu Leu Asp Gly Leu Asp Leu Phe Thr Gly Leu Thr
    1055                1060                1065 atg acg tat acc gac agt cat gcc agc agt aat gca ttc agt ggc        3249
Met Thr Tyr Thr Asp Ser His Ala Ser Ser Asn Ala Phe Ser Gly
    1070                1075                1080 aag acg aag tcc gtc ggg gca ggt ctg tat gct tcc gct ata ttt        3294
Lys Thr Lys Ser Val Gly Ala Gly Leu Tyr Ala Ser Ala Ile Phe
    1085                1090                1095 gac tct ggt gcc tat atc gac ctg att agt aag tat gtt cac cat        3339
Asp Ser Gly Ala Tyr Ile Asp Leu Ile Ser Lys Tyr Val His His
    1100                1105                1110 gat aat gag tac tcg gcg acc ttt gct gga ctc gga aca aaa gac        3384
Asp Asn Glu Tyr Ser Ala Thr Phe Ala Gly Leu Gly Thr Lys Asp
    1115                1120                1125 tac agt tct cat tcc ttg tat gtg ggt gct gaa gca ggc tac cgc        3429
Tyr Ser Ser His Ser Leu Tyr Val Gly Ala Glu Ala Gly Tyr Arg
    1130                1135                1140 tat cat gta aca gaa gac tcc tgg att gag ccg cag gca gaa ctg        3474
Tyr His Val Thr Glu Asp Ser Trp Ile Glu Pro Gln Ala Glu Leu
    1145                1150                1155 gtt tat ggg gcc gta tca ggt aaa cgg ttc gac tgg cag gat cgc        3519
Val Tyr Gly Ala Val Ser Gly Lys Arg Phe Asp Trp Gln Asp Arg
    1160                1165                1170 gga atg agc gtg acc atg aag gat aag gac ttt aat ccg ctg att        3564
Gly Met Ser Val Thr Met Lys Asp Lys Asp Phe Asn Pro Leu Ile
    1175                1180                1185 ggg cgt acc ggt gtt gat gtg ggt aaa tcc ttc tcc ggt aag gac        3609
Gly Arg Thr Gly Val Asp Val Gly Lys Ser Phe Ser Gly Lys Asp
    1190                1195                1200 tgg aaa gtc aca gcc cgc gcc ggc ctt ggc tac cag ttt gac ctg        3654
Trp Lys Val Thr Ala Arg Ala Gly Leu Gly Tyr Gln Phe Asp Leu
    1205                1210                1215 ttt gcc aac ggt gaa acc gta ctg cgt gat gcg tcc ggt gag aaa        3699
Phe Ala Asn Gly Glu Thr Val Leu Arg Asp Ala Ser Gly Glu Lys
    1220                1225                1230 cgt atc aaa ggt gaa aaa gac ggt cgt att ctc atg aat gtt ggt        3744
Arg Ile Lys Gly Glu Lys Asp Gly Arg Ile Leu Met Asn Val Gly
    1235                1240                1245 ctc aac gcc gaa att cgc gat aat ctt cgc ttc ggt ctt gag ttt        3789
Leu Asn Ala Glu Ile Arg Asp Asn Leu Arg Phe Gly Leu Glu Phe
    1250                1255                1260
```

|  |  |  |  |  |  |  |  |  |  |  |  | |
|---|---|---|---|---|---|---|---|---|---|---|---|---|
| gag | aaa | tcg | gca | ttt | ggt | aaa | tac | aac | gtg | gat | aac | gcg atc aac | 3834 |
| Glu | Lys | Ser | Ala | Phe | Gly | Lys | Tyr | Asn | Val | Asp | Asn | Ala Ile Asn |
| 1265 | | | | 1270 | | | | | 1275 | | | |

| gcc | aac | ttc | cgt | tac | tct | ttc | tga | 3858 |
|---|---|---|---|---|---|---|---|---|
| Ala | Asn | Phe | Arg | Tyr | Ser | Phe | | |
| 1280 | | | | | 1285 | | | |

<210> SEQ ID NO 8
<211> LENGTH: 1285
<212> TYPE: PRT
<213> ORGANISM: Shigella flexneri

<400> SEQUENCE: 8

Met Asn Lys Ile Tyr Ser Leu Lys Tyr Ser His Ile Thr Gly Gly Leu
1               5                   10                  15

Val Ala Val Ser Glu Leu Thr Arg Lys Val Ser Val Gly Thr Ser Arg
            20                  25                  30

Lys Lys Val Ile Leu Gly Ile Ile Leu Ser Ser Ile Tyr Gly Ser Tyr
        35                  40                  45

Gly Glu Thr Ala Phe Ala Ala Met Leu Asp Ile Asn Asn Ile Trp Thr
    50                  55                  60

Arg Asp Tyr Leu Asp Leu Ala Gln Asn Arg Glu Phe Arg Pro Gly
65                  70                  75                  80

Ala Thr Asn Val Gln Leu Met Met Lys Asp Gly Lys Ile Phe His Phe
                85                  90                  95

Pro Glu Leu Pro Val Pro Asp Phe Ser Ala Val Ser Asn Lys Gly Ala
            100                 105                 110

Thr Thr Ser Ile Gly Gly Ala Tyr Ser Val Thr Ala Thr His Asn Gly
        115                 120                 125

Thr Gln His His Ala Ile Thr Thr Gln Ser Trp Asp Gln Thr Ala Tyr
    130                 135                 140

Lys Ala Ser Asn Arg Val Ser Ser Gly Asp Phe Ser Val His Arg Leu
145                 150                 155                 160

Asn Lys Phe Val Val Glu Thr Thr Gly Val Thr Glu Ser Ala Asp Phe
                165                 170                 175

Ser Leu Ser Pro Glu Asp Ala Met Lys Arg Tyr Gly Val Asn Tyr Asn
            180                 185                 190

Gly Lys Glu Gln Ile Ile Gly Phe Arg Ala Gly Ala Gly Thr Thr Ser
        195                 200                 205

Thr Ile Leu Asn Gly Lys Gln Tyr Leu Phe Gly Gln Asn Tyr Asn Pro
    210                 215                 220

Asp Leu Leu Ser Ala Ser Leu Phe Asn Leu Asp Trp Lys Asn Lys Ser
225                 230                 235                 240

Tyr Ile Tyr Thr Asn Arg Thr Pro Phe Lys Asn Ser Pro Ile Phe Gly
                245                 250                 255

Asp Ser Gly Ser Gly Ser Tyr Leu Tyr Asp Lys Glu Gln Gln Lys Trp
            260                 265                 270

Val Phe His Gly Val Thr Ser Thr Val Gly Phe Ile Ser Ser Thr Asn
        275                 280                 285

Ile Ala Trp Thr Asn Tyr Ser Leu Phe Asn Asn Ile Leu Val Asn Asn
    290                 295                 300

Leu Lys Lys Asn Phe Thr Asn Thr Met Gln Leu Asp Gly Lys Lys Gln
305                 310                 315                 320

Glu Leu Ser Ser Ile Ile Lys Asp Lys Asp Leu Ser Val Ser Gly Gly
                325                 330                 335

Gly Val Leu Thr Leu Lys Gln Asp Thr Asp Leu Gly Ile Gly Gly Leu

```
                    340             345             350
Ile Phe Asp Lys Asn Gln Thr Tyr Lys Val Tyr Gly Lys Asp Lys Ser
            355                 360                 365
Tyr Lys Gly Ala Gly Ile Asp Ile Asp Asn Asn Thr Thr Val Glu Trp
        370                 375                 380
Asn Val Lys Gly Val Ala Gly Asp Asn Leu His Lys Ile Gly Ser Gly
385                 390                 395                 400
Thr Leu Asp Val Lys Ile Ala Gln Gly Asn Asn Leu Lys Ile Gly Asn
                405                 410                 415
Gly Thr Val Ile Leu Ser Ala Glu Lys Ala Phe Asn Lys Ile Tyr Met
            420                 425                 430
Ala Gly Gly Lys Gly Thr Val Lys Ile Asn Ala Lys Asp Ala Leu Ser
            435                 440                 445
Glu Ser Gly Asn Gly Glu Ile Tyr Phe Thr Arg Asn Gly Gly Thr Leu
        450                 455                 460
Asp Leu Asn Gly Tyr Asp Gln Ser Phe Gln Lys Ile Ala Ala Thr Asp
465                 470                 475                 480
Ala Gly Thr Thr Val Thr Asn Ser Asn Val Lys Gln Ser Thr Leu Ser
                485                 490                 495
Leu Thr Asn Thr Asp Ala Tyr Met Tyr His Gly Asn Val Ser Gly Asn
            500                 505                 510
Ile Ser Ile Asn His Ile Ile Asn Thr Thr Gln Gln His Asn Asn Asn
            515                 520                 525
Ala Asn Leu Ile Phe Asp Gly Ser Val Asp Ile Lys Asn Asp Ile Ser
        530                 535                 540
Val Arg Asn Ala Gln Leu Thr Leu Gln Gly His Ala Thr Glu His Ala
545                 550                 555                 560
Ile Phe Lys Glu Gly Asn Asn Asn Cys Pro Ile Pro Phe Leu Cys Gln
                565                 570                 575
Lys Asp Tyr Ser Ala Ala Ile Lys Asp Gln Glu Ser Thr Val Asn Lys
            580                 585                 590
Arg Tyr Asn Thr Glu Tyr Lys Ser Asn Asn Gln Ile Ala Ser Phe Ser
            595                 600                 605
Gln Pro Asp Trp Glu Ser Arg Lys Phe Asn Phe Arg Lys Leu Asn Leu
        610                 615                 620
Glu Asn Ala Thr Leu Ser Ile Gly Arg Asp Ala Asn Val Lys Gly His
625                 630                 635                 640
Ile Glu Ala Lys Asn Ser Gln Ile Val Leu Gly Asn Lys Thr Ala Tyr
                645                 650                 655
Ile Asp Met Phe Ser Gly Arg Asn Ile Thr Gly Glu Gly Phe Gly Phe
            660                 665                 670
Arg Gln Gln Leu Arg Ser Gly Asp Ser Ala Gly Glu Ser Ser Phe Asn
            675                 680                 685
Gly Ser Leu Ser Ala Gln Asn Ser Lys Ile Thr Val Gly Asp Lys Ser
        690                 695                 700
Thr Val Thr Met Thr Gly Ala Leu Ser Leu Ile Asn Thr Asp Leu Ile
705                 710                 715                 720
Ile Asn Lys Gly Ala Thr Val Thr Ala Gln Gly Lys Met Tyr Val Asp
                725                 730                 735
Lys Ala Ile Glu Leu Ala Gly Thr Leu Thr Leu Thr Gly Thr Pro Thr
            740                 745                 750
Glu Asn Asn Lys Tyr Ser Pro Ala Ile Tyr Met Ser Asp Gly Tyr Asn
            755                 760                 765
```

-continued

Met Thr Glu Asp Gly Ala Thr Leu Lys Ala Gln Asn Tyr Ala Trp Val
770                 775                 780

Asn Gly Asn Ile Lys Ser Asp Lys Lys Ala Ser Ile Leu Phe Gly Val
785                 790                 795                 800

Asp Gln Tyr Lys Glu Asp Asn Leu Asp Lys Thr Thr His Thr Pro Leu
            805                 810                 815

Ala Thr Gly Leu Leu Gly Gly Phe Asp Thr Ser Tyr Thr Gly Gly Ile
        820                 825                 830

Asp Ala Pro Ala Ala Ser Ala Ser Met Tyr Asn Thr Leu Trp Arg Val
    835                 840                 845

Asn Gly Gln Ser Ala Leu Gln Ser Leu Lys Thr Arg Asp Ser Leu Leu
850                 855                 860

Leu Phe Ser Asn Ile Glu Asn Ser Gly Phe His Thr Val Thr Val Asn
865                 870                 875                 880

Thr Leu Asp Ala Thr Asn Thr Ala Val Ile Met Arg Ala Asp Leu Ser
            885                 890                 895

Gln Ser Val Asn Gln Ser Asp Lys Leu Ile Val Lys Asn Gln Leu Thr
        900                 905                 910

Gly Ser Asn Asn Ser Leu Ser Val Asp Ile Gln Lys Val Gly Asn Asn
    915                 920                 925

Asn Ser Gly Leu Asn Val Asp Leu Ile Thr Ala Pro Lys Gly Ser Asn
930                 935                 940

Lys Glu Ile Phe Lys Ala Ser Thr Gln Ala Ile Gly Phe Ser Asn Ile
945                 950                 955                 960

Ser Pro Val Ile Ser Thr Lys Glu Asp Gln Glu His Thr Thr Trp Thr
            965                 970                 975

Leu Thr Gly Tyr Lys Val Ala Glu Asn Thr Ala Ser Ser Gly Ala Ala
        980                 985                 990

Lys Ser Tyr Met Ser Gly Asn Tyr Lys Ala Phe Leu Thr Glu Val Asn
    995                 1000                1005

Asn Leu Asn Lys Arg Met Gly Asp Leu Arg Asp Thr Asn Gly Glu
1010                1015                1020

Ala Gly Ala Trp Ala Arg Ile Met Ser Gly Ala Gly Ser Ala Ser
1025                1030                1035

Gly Gly Tyr Ser Asp Asn Tyr Thr His Val Gln Ile Gly Val Asp
1040                1045                1050

Lys Lys His Glu Leu Asp Gly Leu Asp Leu Phe Thr Gly Leu Thr
1055                1060                1065

Met Thr Tyr Thr Asp Ser His Ala Ser Ser Asn Ala Phe Ser Gly
1070                1075                1080

Lys Thr Lys Ser Val Gly Ala Gly Leu Tyr Ala Ser Ala Ile Phe
1085                1090                1095

Asp Ser Gly Ala Tyr Ile Asp Leu Ile Ser Lys Tyr Val His His
1100                1105                1110

Asp Asn Glu Tyr Ser Ala Thr Phe Ala Gly Leu Gly Thr Lys Asp
1115                1120                1125

Tyr Ser Ser His Ser Leu Tyr Val Gly Ala Glu Ala Gly Tyr Arg
1130                1135                1140

Tyr His Val Thr Glu Asp Ser Trp Ile Glu Pro Gln Ala Glu Leu
1145                1150                1155

Val Tyr Gly Ala Val Ser Gly Lys Arg Phe Asp Trp Gln Asp Arg
1160                1165                1170

Gly Met Ser Val Thr Met Lys Asp Lys Asp Phe Asn Pro Leu Ile
1175                1180                1185

-continued

Gly Arg Thr Gly Val Asp Gly Lys Ser Phe Ser Gly Lys Asp
        1190              1195              1200

Trp Lys Val Thr Ala Arg Ala Gly Leu Gly Tyr Gln Phe Asp Leu
    1205              1210              1215

Phe Ala Asn Gly Glu Thr Val Leu Arg Asp Ala Ser Gly Glu Lys
    1220              1225              1230

Arg Ile Lys Gly Glu Lys Asp Gly Arg Ile Leu Met Asn Val Gly
    1235              1240              1245

Leu Asn Ala Glu Ile Arg Asp Asn Leu Arg Phe Gly Leu Glu Phe
    1250              1255              1260

Glu Lys Ser Ala Phe Gly Lys Tyr Asn Val Asp Asn Ala Ile Asn
    1265              1270              1275

Ala Asn Phe Arg Tyr Ser Phe
    1280              1285

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccggaattcg gagtgaaaac gggggagc                                    29

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggcggctcg agctagtggt ggtggtggtg gtgaatactt gcactatttt t          51

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccggggaat tcgggaaaaa gccttcaata aaa                              33

<210> SEQ ID NO 12
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cggcggctcg agctagtggt ggtggtggtg gtggttgaaa ctactttcgc ctg         53

<210> SEQ ID NO 13
<211> LENGTH: 32
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 13
cccggggaat tcaccactaa ctatccactt tt                                    32

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggcggctcg agctagtggt ggtggtggtg gtgactgtaa cgactctctt ggta            54

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggctctagaa ccactaacta tccactt                                          27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccgaattcc cagctctggt cggtcca                                          27

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggctctagag aactgacccg gaaagttagt                                       30

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccgaattcg tacgcacctc ctaatga                                          27

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
cccggggaat tcggtatggc gaaacagcat ttgc                          34

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggcggctcg agctagtggt ggtggtggtg gtgctcttgt tttttaccat cca     53

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccggggaagc ttgaccccta cagaaaataa ta                            32

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggcggctcg agctagtggt ggtggtggtg gtgctcgcca ttggtgtcac gca     53

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccggggaat tcgggataaa aaacatgagc tgg                           33

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cggcggctcg agctagtggt ggtggtggtg gtggaaagag taacggaagt tgg     53
```